(12) United States Patent
Yokoyama et al.

(10) Patent No.: US 11,918,717 B2
(45) Date of Patent: Mar. 5, 2024

(54) BLOOD PURIFICATION DEVICE

(71) Applicant: NIKKISO CO., LTD., Tokyo (JP)

(72) Inventors: Takayoshi Yokoyama, Makinohara (JP); Masato Fujiwara, Makinohara (JP); Hiroshi Nimura, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 413 days.

(21) Appl. No.: 17/269,856

(22) PCT Filed: Aug. 27, 2019

(86) PCT No.: PCT/JP2019/033425
§ 371 (c)(1),
(2) Date: Feb. 19, 2021

(87) PCT Pub. No.: WO2020/045385
PCT Pub. Date: Mar. 5, 2020

(65) Prior Publication Data
US 2021/0170085 A1 Jun. 10, 2021

(30) Foreign Application Priority Data
Aug. 27, 2018 (JP) .................. 2018-158144

(51) Int. Cl.
*A61M 1/16* (2006.01)
*A61M 1/14* (2006.01)
*A61M 1/36* (2006.01)

(52) U.S. Cl.
CPC .......... *A61M 1/1629* (2014.02); *A61M 1/152* (2022.05); *A61M 1/153* (2022.05);
(Continued)

(58) Field of Classification Search
CPC ...... A61M 1/152; A61M 1/153; A61M 1/155; A61M 1/1562; A61M 1/15632; A61M 1/16; A61M 1/1629; A61M 1/1696; A61M 1/341; A61M 1/36222; A61M 1/36223; A61M 1/36225; A61M 1/362262;
(Continued)

(56) References Cited

U.S. PATENT DOCUMENTS 4,661,246 A 4/1987 Ash
5,578,223 A 11/1996 Bene et al.
(Continued)

FOREIGN PATENT DOCUMENTS

CN 101610799 A 12/2009
CN 101868260 A 10/2010
(Continued)

OTHER PUBLICATIONS

Jan. 31, 2023 Office Action issued in Japanese Patent Application No. 2020-539466.
(Continued)

*Primary Examiner* — Dirk R Bass
(74) *Attorney, Agent, or Firm* — Oliff PLC

(57) ABSTRACT

A blood purification device includes a device body and a cassette. The cassette includes: a casing that accommodates a removal water receptacle; and pump tube. The device body includes fingers, a driving unit, and a housing. The cassette can be attached to and removed from the housing of the device body so that the pump tubes are positioned between the plurality of fingers and the outer surfaces of the casing.

14 Claims, 19 Drawing Sheets

(52) U.S. Cl.
CPC ......... *A61M 1/155* (2022.05); *A61M 1/1562* (2022.05); *A61M 1/15632* (2022.05); *A61M 1/36222* (2022.05); *A61M 1/36223* (2022.05); *A61M 1/36225* (2022.05); *A61M 1/362262* (2022.05)

(58) Field of Classification Search
CPC ...... A61M 2205/123; A61M 2205/125; A61M 2205/332; A61M 2205/3393
See application file for complete search history.

(56) References Cited

U.S. PATENT DOCUMENTS

| | | |
|---|---|---|
| 6,824,524 B1 | 11/2004 | Favre |
| 2009/0101566 A1 | 4/2009 | Crnkovich et al. |
| 2010/0087771 A1 | 4/2010 | Karakama et al. |
| 2012/0091053 A1 | 4/2012 | Crnkovich et al. |
| 2014/0083944 A1 | 3/2014 | Childers et al. |

FOREIGN PATENT DOCUMENTS

| | | |
|---|---|---|
| JP | S61-119275 A | 6/1986 |
| JP | H06-030993 A | 2/1994 |
| JP | 2003-010316 A | 1/2003 |
| JP | 2007-097746 A | 4/2007 |
| JP | 5657726 B2 | 1/2015 |
| WO | 2008/099890 A1 | 8/2008 |

OTHER PUBLICATIONS

Apr. 25, 2022 Search Report issued in European Patent Application No. 19853863.9.

Mar. 17, 2023 Office Action issued in Chinese Patent Application No. 201980055485.5.

Nov. 5, 2019 Search Report issued in International Patent Application No. PCT/JP2019/033425.

Aug. 28, 2020 International Preliminary Report on Patentability issued in International Patent Application No. PCT/JP2019/033425.

BLOOD PURIFICATION DEVICE

CROSS-REFERENCE TO RELATED APPLICATION

This application is a National Stage of PCT international application Ser. No. PCT/JP2019/033425 filed on Aug. 27, 2019 which designates the United States, and also claims priority to Japanese Patent Application No. 2018-158144 filed on Aug. 27, 2018, incorporated herein by reference.

TECHNICAL FIELD

The present invention relates to a configuration of a blood purification device.

BACKGROUND

To facilitate handling of blood purification devices, there is proposed a blood purification device including a body including a pump rotor and a controller, and a cassette housing a dialyzer, pump tubes, a blood loop, and other components and removably assembled to the body. This blood purification device is configured such that, when the cassette is assembled to the body, the pump tubes in the cassette are sequentially squeezed by the pump rotor in the body to pressure-feed blood and dialysate, for example, to the dialyzer (see Patent Document 1, for example).

During dialysis, water removal is performed to remove excessive water out of the patient's body. As the feed amounts of a blood pump and a dialysate pump need to be controlled based on the amount of removed water, it is necessary to store the removed water in a bag and measure the amount of removed water. To this end, the weight of the bag placed outside the blood purification device is measured to thereby determine the amount of removed water (see Patent Document 2, for example).

CITATION LIST

Patent Literature

[Patent Document 1] JP 2007-97746 A
[Patent Document 2] JP 5657726 B

SUMMARY

Technical Problem

While the conventional blood purification device disclosed in Patent Document 1 partially houses wet parts within the cassette, some wet parts such as a removed water container, for example, need to be separately attached to the blood purification device as described in Patent Document 2. Further simplification of handling of blood purification devices is therefore required.

The present invention is therefore aimed at simplification of handling of blood purification devices.

Solution to Problem

A blood purification device according to the present invention includes a device body, and a cassette to be removably assembled to the device body. The cassette includes a casing that houses a removed water container, and the cassette is attachable and removable with respect to the device body.

The removed water container mounted in the cassette can be thus integrally assembled to the device body removably, which simplifies handling of the blood purification device.

The blood purification device according to the present invention may further include a load detector mounted on the device body and configured to measure a load of the removed water container, and a load transmission mechanism configured to transmit to the load detector the load of the removed water container housed in the cassette.

This configuration enables measurement of the weight of the removed water container housed in the cassette by the device body housing the load detector, thereby simplifying handling of the blood purification device.

In the blood purification device according to the present invention, the load transmission mechanism may include a hole in a bottom board of the cassette in a portion where the removed water container is housed, and the removed water container may be configured to be placed on or above the load detector. The device body may include a base on which the load detector is mounted, and the load detector may be inserted through the hole. The device body may further include a cassette seat configured to receive the cassette. The load transmission mechanism may include the hole, and an opening in the cassette seat at a location corresponding to the hole in the cassette, and the load detector may be inserted through the hole and the opening.

This simple configuration enables measurement of the weight of the removed water container housed in the cassette by the device body that houses the load detector.

In the blood purification device according to the present invention, the device body may include a base on which the load detector is mounted. The load transmission mechanism may include the hole, and a spacer inserted through the hole. The spacer may be sandwiched between the load detector mounted on the base and a bottom face of the removed water container to thereby lift the removed water container up off a bottom board of the cassette. The removed water container may be configured to be placed on the spacer on top of the load detector. Further, the device body may include a cassette seat configured to receive the cassette and disposed with an interval from the base. The load transmission mechanism may further include an opening in the cassette seat at a location corresponding to the hole of the cassette, and the spacer may be inserted through the hole and the opening and sandwiched between the load detector mounted on the base and a bottom face of the removed water container to thereby lift the removed water container up off the bottom board of the cassette that is assembled to the device body to bring the bottom face of the cassette into contact with the cassette seat of the device body.

This simple configuration enables measurement of the weight of the removed water container housed in the cassette by the device body that houses the load detector.

In the blood purification device according to the present invention, the load transmission mechanism may include an opening in a top board of the cassette in a portion where the removed water container is housed, and an engaging unit protruding on an upper portion of the removed water container, and the removed water container may be suspended from the load detector. Further, the load transmission mechanism may include a connector coupled with the load detector mounted on the device body, which is configured to engage the engaging unit of the removed water container through the opening to lift the removed water container up off a bottom board of the cassette assembled to the device body, and the removed water container may be suspended from the load detector via the connector.

This simple configuration enables measurement of the weight of the removed water container housed in the cassette by the device body that houses the load detector.

In the blood purification device according to the present invention, the device body may include a heater disposed such that part or all of the heater enters the interior of the cassette that is assembled to the device body. For example, the heater may be disposed in a region under the removed water container housed in the cassette when the cassette is assembled to the device body, such that part or all of the heater enters the interior of the cassette from below. Further, the removed water container may include a recess portion in its bottom such that, when the cassette is assembled to the device body, the heater may enter the recess portion from below. Also, the heater may be inserted into the interior of the cassette from the side of the cassette or from above the cassette.

In the blood purification device according to the present invention, the device body may include a heater to be disposed near the cassette that is assembled to the device body. For example, the device body may include the heater to be located near a region under the cassette when the cassette is assembled to the device body. The device body may include the heater to be located adjacent to a side face of the cassette when the cassette is assembled to the device body. The device body may include the heater to be located near a region above the cassette when the cassette is assembled.

This simple configuration enables measurement of the weight of the removed water container housed in the cassette by the device body that houses the load detector and also enables heating of the dialysate to thereby maintain the temperature of blood to be reinfused to the patient.

In the blood purification device according to the present invention, the cassette may further house a dialyzer and a dialysate regeneration column. Further, the blood purification device according to the present invention may further include a pump unit including an elastic pump tube, a tube receiver configured to receive the pump tube, a tube pressing member configured to press a portion of the pump tube onto the tube receiver, and a driver unit configured to move the tube pressing member along a longitudinal direction of the pump tube, and configured to squeeze out liquid within the pump tube. In the blood purification device, the cassette may include at least a portion of the pump unit, and the device body may include a further portion of the pump unit. Here, the cassette may include the tube receiver and the pump tube of the pump unit, and the device body may include the tube pressing member and the driver unit. The tube receiver may be the casing of the cassette, and the pump tube may be mounted on an outer face of the casing. The tube pressing member may include a plurality of fingers, and the cassette may be attachable and removable with respect to the device body such that the pump tube is located between the fingers and the outer face of the casing. Further, here, the cassette may include the tube receiver, the pump tube, and the tube pressing member of the pump unit, and the device body may include the driver unit. The tube pressing member may be a rotor. The pump tube may include an arc portion along an outer circumference of the rotor. The tube receiver may be a stator including an arc portion along an outer circumference of the pump tube. The cassette may be attachable and removable with respect to the device body such that the rotor engages the driver unit when the cassette is assembled to the device body and the rotor is separated from the driver unit when the cassette is removed from the device body.

This configuration enables all of wet parts to be integrally assembled or removed with respect to the device body to thereby simplify handling of the blood purification device.

Advantageous Effects of Invention

The present invention simplifies handling of blood purification devices.

DESCRIPTION OF EMBODIMENTS

Figure 1:
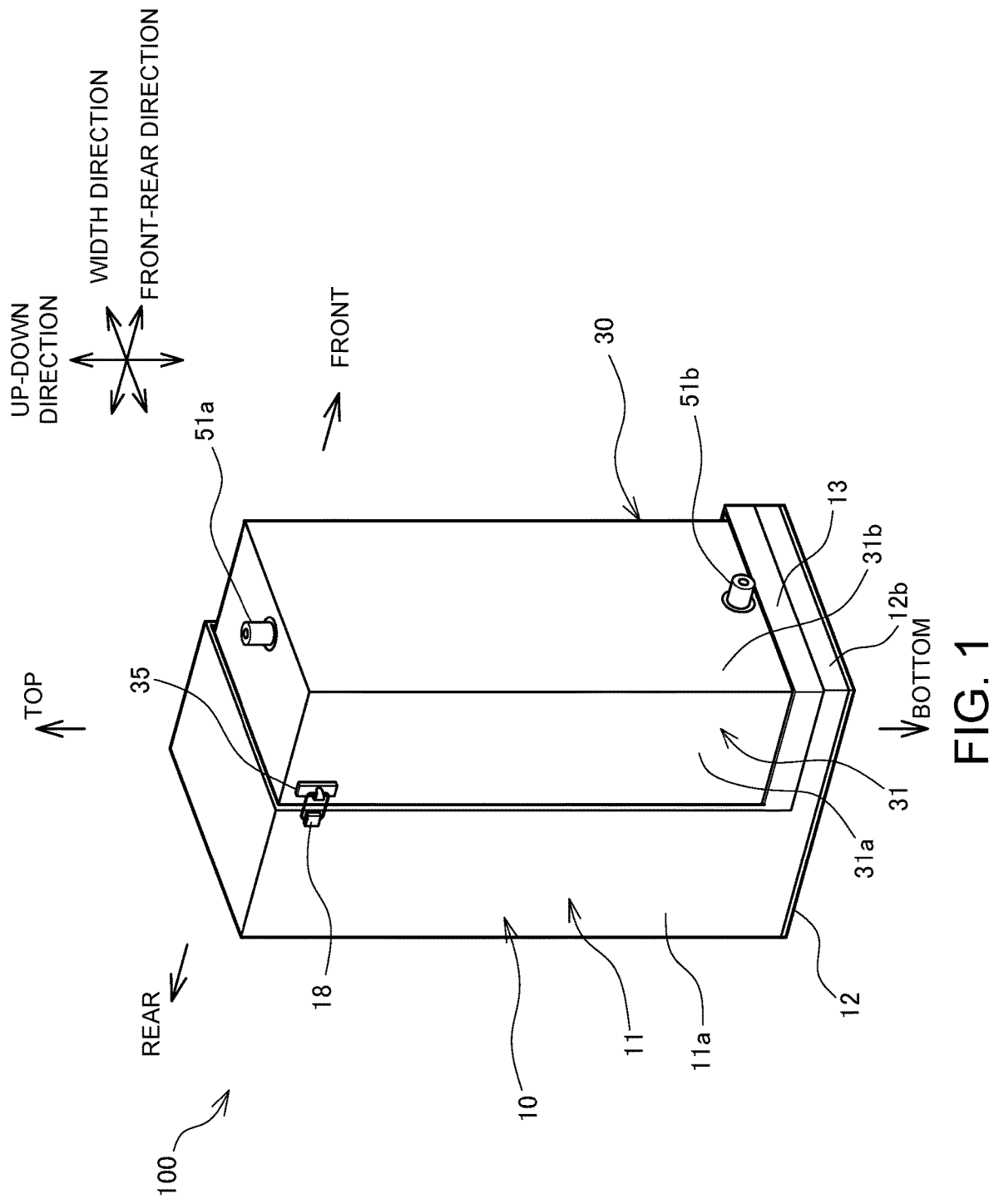
FIG. 1 is a perspective view of a blood purification device according to an embodiment.

A blood purification device 100 according to an embodiment will be described by reference to the drawings. As illustrated in FIG. 1, the blood purification device 100 includes a device body 10, and a cassette 30 removably assembled to the device body 10. The cassette 30 is assembled to the device body 10 with a lower part of the cassette 30 fitted in a cassette seat 13 of the device body 10 and a hook 35 in an upper part of the cassette 30 fastened with a fitting 18 of the device body 10. For use in dialysis, for example, a blood inlet nozzle 51a and a blood outlet nozzle 51b of the cassette 30 are respectively coupled with blood vessels of a patient's body. In the following description, the direction in which the device body 10 and the cassette 30 are arranged is referred to as a front-rear direction, the direction orthogonal to the front-rear direction in a horizontal plane as a width direction, and the vertical direction as an up-down direction.

Figure 2:
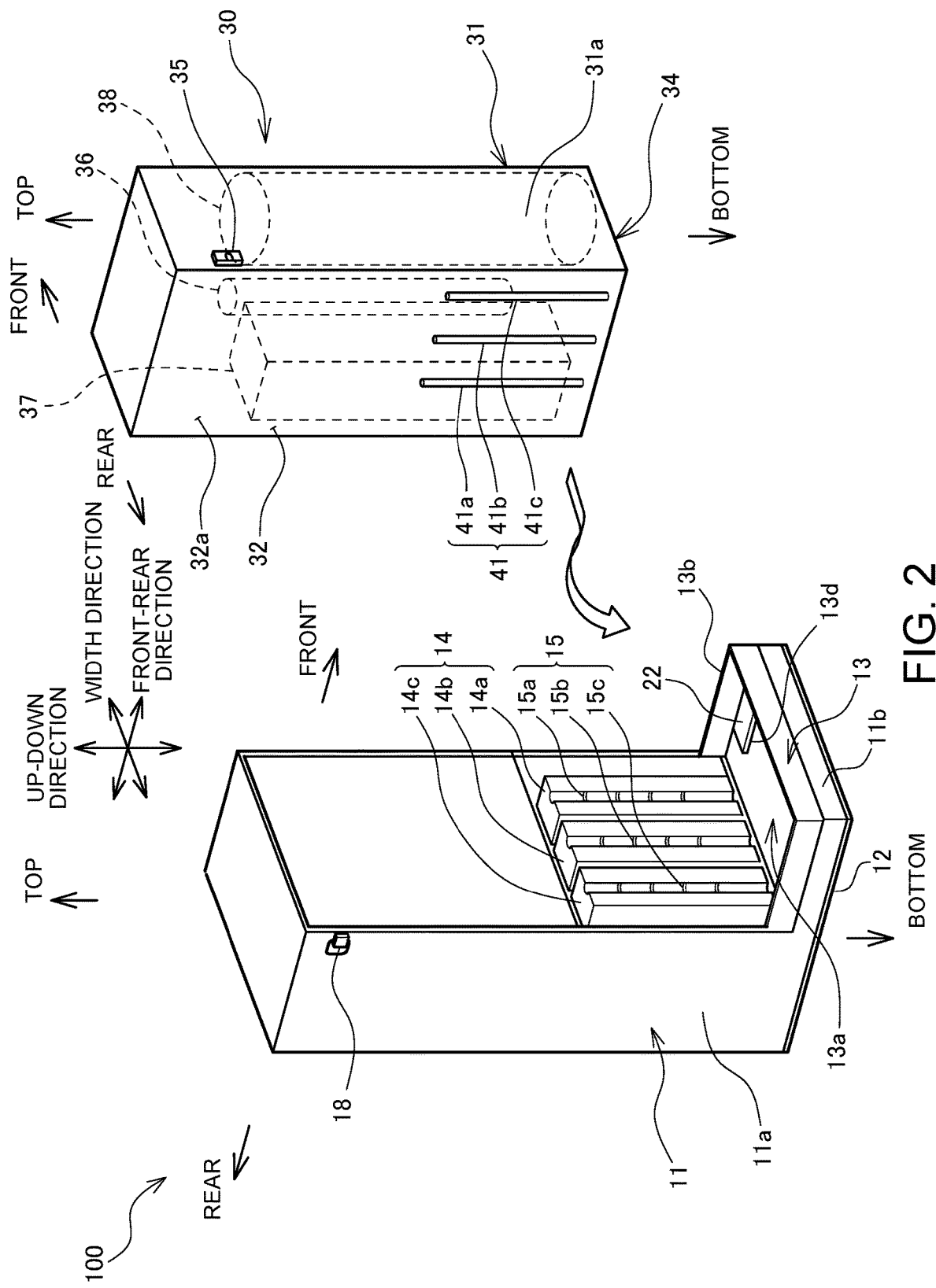
FIG. 2 is an exploded perspective view of the blood purification device according to the embodiment.
Figure 3:
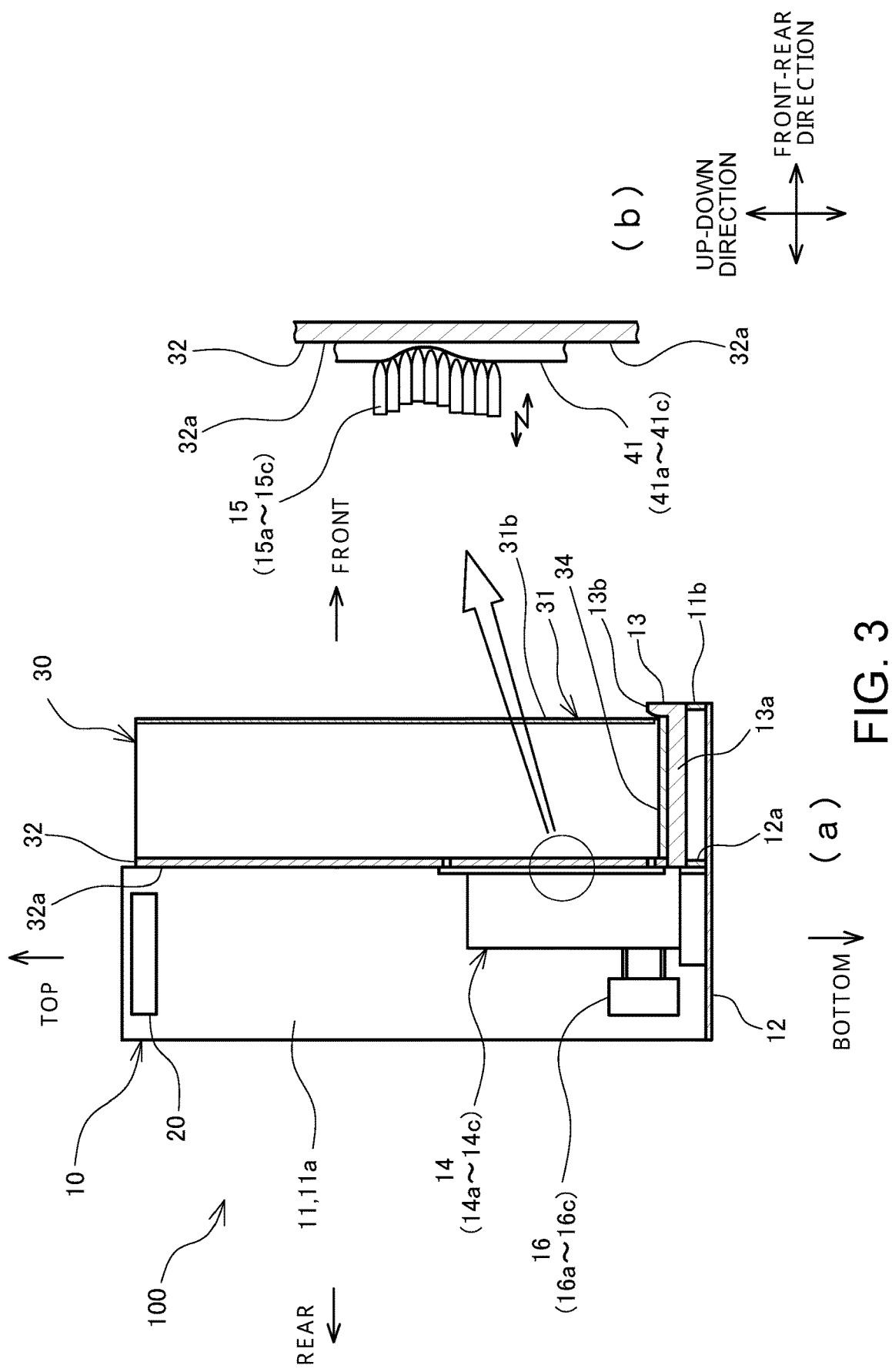
FIG. 3 is a vertical cross section of the blood purification device according to the embodiment.

As illustrated in FIG. 2, the cassette 30 includes a casing 31 that houses a dialyzer 36, a dialysate regeneration column 38, and a removed water container 37, and the casing 31 includes, on an outer face 32a of its rear board 32, a plurality of elastic pump tubes 41 (41a to 41c). The casing 31 forms a tube receiver that receives the pump tubes 41. As illustrated in FIG. 3, the device body 10 includes a finger casing 14 storing a plurality of fingers 15, driver units 16 of the fingers 15, a controller 20 that performs driving control of the driver units 16, and a housing 11 that houses these elements. The fingers 15 are tube pressing members that compress the pump tubes 41 radially while moving the compressing position along the longitudinal direction of the pump tubes 41 to thereby allow the interior liquid to flow. The fingers 15 and the finger casings 14 form a peristaltic pump that is a pump unit.

The blood purification device 100 includes a blood loop and a dialysate loop. The blood loop is a liquid loop that returns blood of a human body flowing from the blood inlet nozzle 51a back to the human body through the blood outlet nozzle 51b, and includes the pump tube 41a of the blood pump, a blood flow channel of the dialyzer 36, a drip chamber, and a coupling tube that couples these elements together. The dialysate loop is a liquid loop that circulates the dialysate in the dialyzer 36, and includes a dialysate fluid channel of the dialyzer 36, the dialysate regeneration column 38, the removed water container 37, the pump tube 41b of a dialysate outlet pump, the pump tube 41c of a dialysate inlet pump, and a coupling tube that couples these elements. The dialysate regeneration column 38 may be disposed anywhere within the dialysate loop.

The blood purification device 100 allows blood to flow through the blood loop and allows dialysate to flow through the dialysate loop to remove unnecessary waste and excess water out of the blood by the dialyzer 36. The blood loop and the dialysate loop form wet parts. As illustrated in FIGS. 1 and 2, the cassette 30 includes the dialyzer 36, the dialysate regeneration column 38, the removed water container 37, a drip chamber, the pump tubes 41a to 41c, the blood inlet nozzle 51a, the blood outlet nozzle 51b, and the coupling tubes coupling these elements.

While in the description, the pump tubes 41a to 41c correspond to the blood pump, the dialysate outlet pump, and the dialysate inlet pump, respectively, the pump tubes 41a to 41c may be included in any of the blood pump, the dialysate outlet pump, and the dialysate inlet pump.

As illustrated in FIG. 2, the housing 11 of the device body 10 includes a base 12 that is a rectangular board, right and left L-shape side boards 11a, a front board 11b attached at the front of the base 12, and the cassette seat 13. As illustrated in FIG. 3(a), the base 12 includes a rib 12a in its center, and the cassette seat 13 is mounted on the front portions of the right and left side boards 11a, the front board 11b, and the rib 12a. As such, the cassette seat 13 is assembled to the base 12 with an interval between the cassette seat 13 and the base 12.

Figure 5:
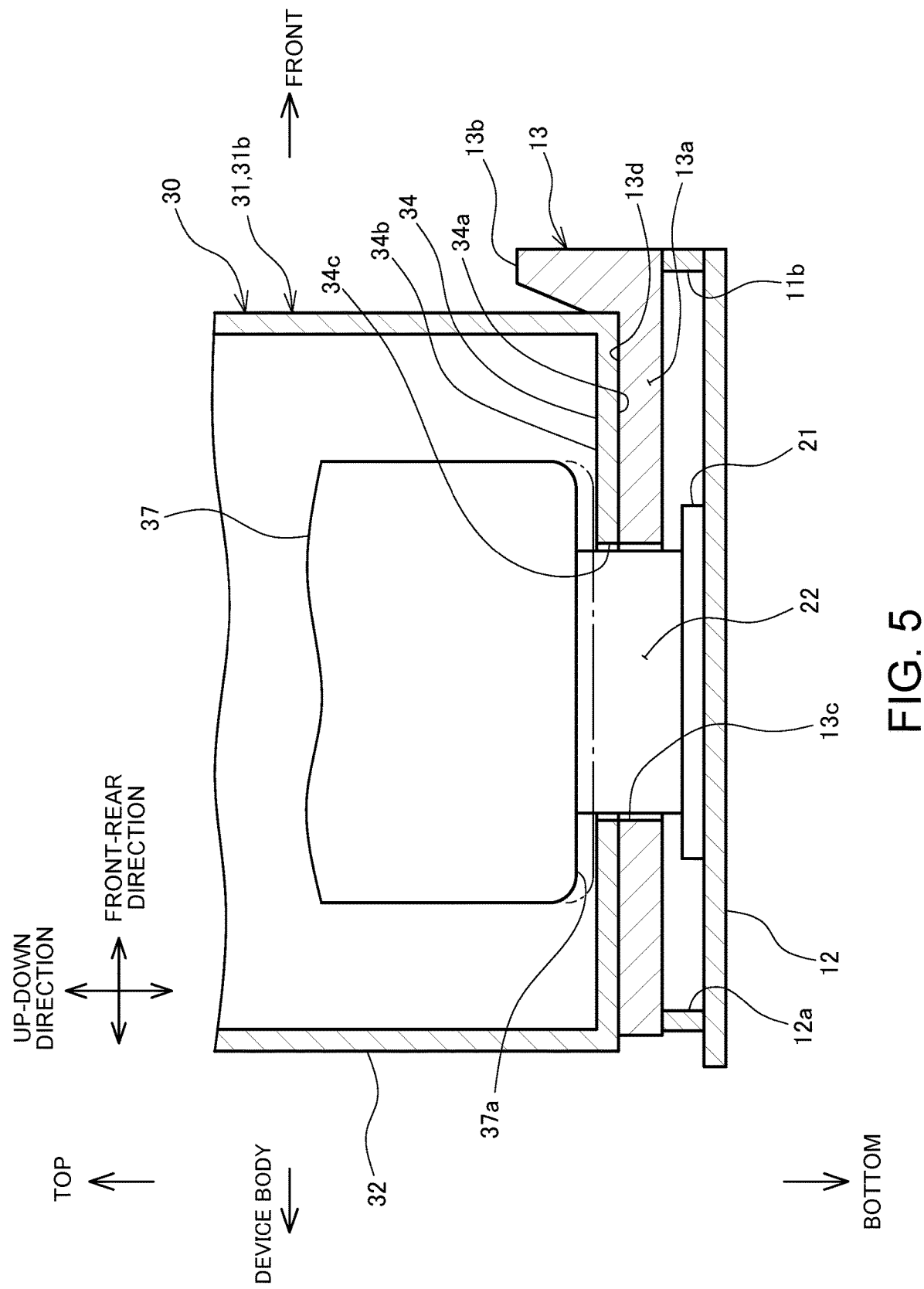
FIG. 5 is a cross section taken along line A-A shown in FIG. 4.

As illustrated in FIGS. 2 and 3, the cassette seat 13 includes a flat receiving board 13a mounted on the front portion of the right and left side boards 11a, the front board 11b, and the rib 12a and receiving a bottom board 34 of the cassette 30, and a vertical flange 13b raising on opposite widthwise ends and the front end of the receiving board 13a. An inner face of the vertical flange 13b is sloped outward to facilitate receiving of the cassette 30, as illustrated in FIG. 5.

The finger casings 14a to 14c forming the blood pump, the dialysate outlet pump, and the dialysate inlet pump, respectively, are mounted on an upper face of the base 12. Each of driver units 16a to 16c is attached to the corresponding one of the finger casings 14a to 14c.

As illustrated in FIGS. 2 and 3(a), the casing 31 of the cassette 30 includes the bottom board 34, the rear board 32 raising vertically from a rear edge of the bottom board 34, side boards 31a raising vertically from opposite widthwise edges of the bottom board 34, and a front board 31b raising vertically from a front edge of the bottom board 34. The dialyzer 36, the dialysate regeneration column 38, and the removed water container 37 are housed within a space enclosed by the bottom board 34, the side boards 31a, the front board 31b, and the rear board 32. The coupling tube coupling the dialyzer 36, the dialysate regeneration column 38, and the removed water container 37 is also housed within the cassette 30.

The pump tubes 41a to 41c are attached on a flat outer face 32a of the rear board 32 adjacent to the device body. The pump tubes 41a to 41c are coupled to the blood loop and the dialysate loop at their opposite ends. The pump tubes 41a to 41c have faces adjacent to the rear board 32 that are disposed along the flat outer face 32a of the rear board 32.

Figure 4:
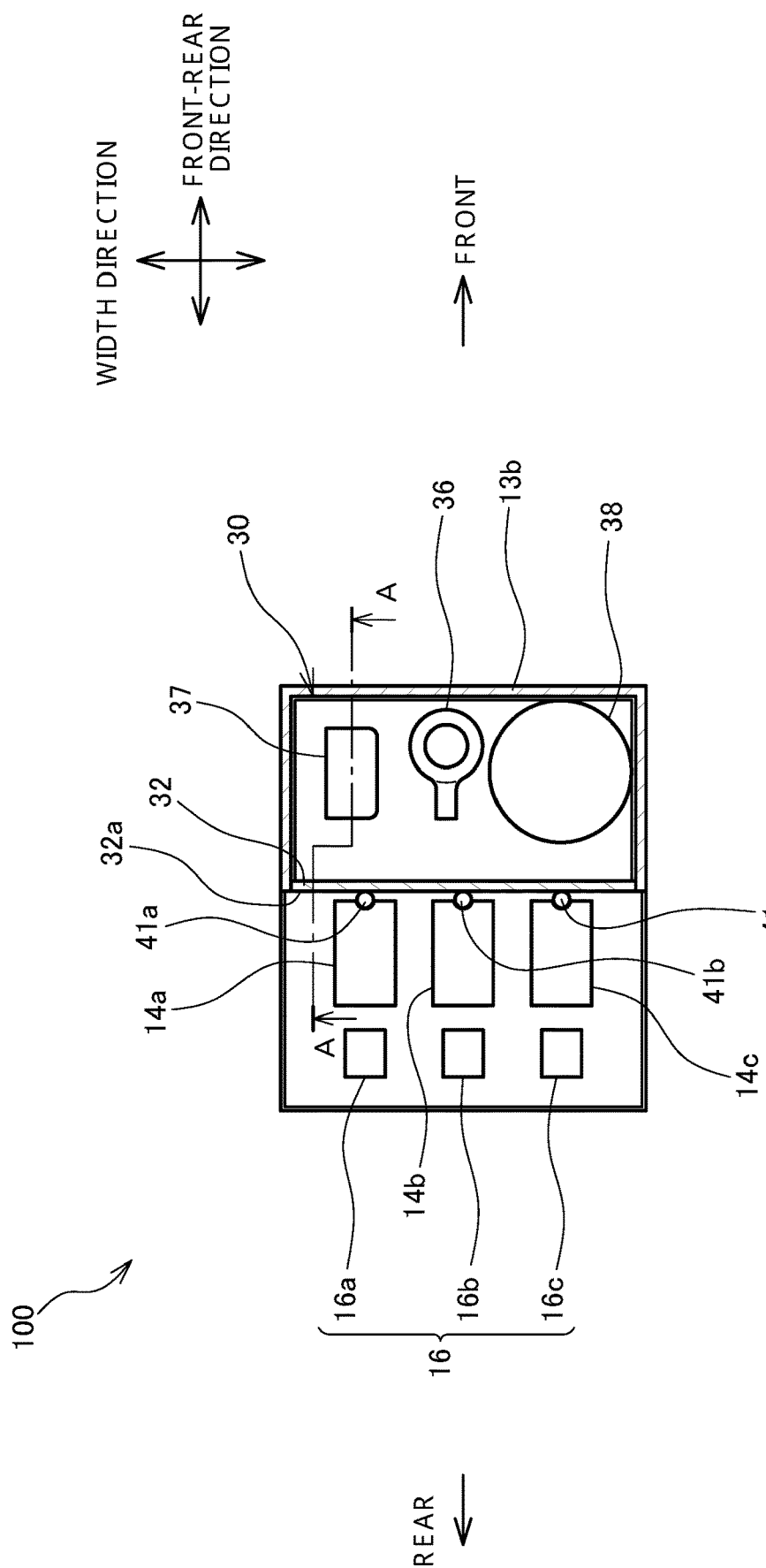
FIG. 4 is a horizontal cross section of the blood purification device according to the embodiment.

As illustrated in FIG. 2, each of the finger casings 14a to 14c includes, on a frontward face, a vertically extending slot into which the corresponding one of the pump tubes 41a to 41c is fit. On assembling the cassette 30 to the device body 10, with the rear board 32 of the cassette 30 facing the device body 10 as illustrated in FIG. 2, the pump tubes 41a to 41c are located between the slots of the corresponding finger casings 14a to 14c and the flat outer face 32a of the rear board 32, as illustrated in FIG. 4. Upon being driven by the corresponding driver units 16a to 16c, respectively, the fingers 15a to 15c press the elastic pump tubes 41a to 41c, respectively, as illustrated in FIG. 3(b).

FIG. 5 is a cross section of a portion of the cassette 30 where the removed water container 37 is housed, taken along line A-A in FIG. 4. As illustrated in FIG. 5, the cassette 30 includes a hole 34c in a region of the bottom board 34 where the removed water container 37 is housed. Meanwhile, the cassette seat 13 also includes an opening 13c at a location corresponding to the hole 34c formed on the bottom board 34 of the cassette 30. The hole 34c and the opening 13c together form a single through hole through which a spacer 22 is inserted. A load detector 21 that measures the load of the removed water container 37 is disposed on an upper face of the base 12 under the spacer 22. The spacer 22 has such a thickness that allows the spacer 22 to protrude from an upper face 34b of the bottom board 34 to lift the bottom face 37a of the removed water container 37 up off the upper face 34b of the bottom board 34, when the cassette 30 is assembled to the device body 10 to bring an undersurface 34a of the bottom board 34 into contact with an upper face 13d of the cassette seat 13.

As indicated by a dashed and single-dotted line in FIG. 5, prior to assembling the cassette 30 to the device body 10, the load of the removed water container 37 is supported by the upper face 34b of the bottom board 34 of the casing 31. In assembling the cassette 30 to the housing 11 of the device body 10 to bring the undersurface 34a of the bottom board 34 closer to the upper face 13d of the cassette seat 13, the upper face of the spacer 22 starts protruding through the upper face 34b of the bottom board 34. Then, after the cassette 30 is assembled to the housing 11 of the device body 10 to bring the undersurface 34a of the bottom board 34 in contact with the upper face 13d of the cassette seat 13, the upper face of the spacer 22 protrudes through the upper face 34b of the bottom board 34 to lift the bottom face 37a of the removed water container 37 up off the upper face 34b of the bottom board 34, as indicated by a solid line in FIG. 5. The spacer 22 is sandwiched between the load detector 21 and the bottom face 37a of the removed water container 37 to transmit the load of the removed water container 37 to the load detector 21. As described, the load detector 21 disposed on the device body 10 is capable of measuring the load of the removed water container 37 housed within the cassette 30 and placed above the load detector 21. As such, the load detector 21 measures the load of the removed water container 37 containing liquid, not the weight of the whole cassette 30, which allows accurate measurement of the load of the removed water container 37.

The hole 34c formed in the bottom board 34 of the cassette 30, the opening 13c formed in the cassette seat 13, and the spacer 22 inserted through the hole 34c and the opening 13c form a load transmission mechanism that transmits the load of the removed water container 37 to the load detector 21.

While in the above description, the load detector 21 and the spacer 22 are separate elements, other configurations may be employed. For example, the load detector 21 may be configured to be inserted through the hole 34c formed in the bottom board 34 of the cassette 30 and the opening 13c formed in the cassette seat 13 such that, when the cassette 30 is assembled to the housing 11 of the device body 10, the upper face of the load detector 21 protrudes through the upper face 34b of the bottom board 34 to allow the removed water container 37 to be placed directly on the load detector 21.

A configuration without the cassette seat 13 may also be employed. Specifically, the base 12 may have a recess in a region corresponding to the hole 34c formed in the bottom board 34 of the cassette 30 to allow the load detector 21 to be mounted in the recess and to be inserted through the hole 34c such that, when the cassette 30 is assembled to the housing 11 of the device body 10, the upper face of the load detector 21 protrudes through the upper face 34b of the bottom board 34 and the removed water container 37 is placed on the load detector 21.

The above configuration may be further modified such that the spacer 22 is superposed on the load detector 21, and, when the cassette 30 is assembled to the housing 11 of the device body 10, the upper face of the spacer 22 protrudes through the upper face 34b of the bottom board 34 to allow the removed water container 37 to be placed on the spacer 22.

As described above, in the blood purification device 100 according to the embodiment, the cassette 30 collectively houses the dialyzer 36, the removed water container 37, the dialysate regeneration column 38, and the pump tubes 41a to 41c and the coupling tubes that couple these elements, that form the blood loops and the dialysate loop, and the cassette 30 is removably assembled to the device body 10. This configuration enables dialysis to be performed only by assembling the cassette 30 to the device body 10 and connecting the blood inlet nozzle 51a and the blood outlet nozzle 51b with a puncture needle inserted in the blood vessel of a patient's body, which simplifies handling of the blood purification device 100. The cassette 30 that contains all of disposable components of the wet parts of the blood loop and the dialysate loop may be disposable, which allows disposal of these disposable components collectively. This also simplifies handling of the blood purification device 100.

In the description of the blood purification device 100 according to this embodiment, the fingers 15 are the tube pressing elements of the pump unit, and the casing 31 is the tube receiver, and the pump is a peristaltic pump that presses the pump tubes 41 radially while shifting the pressing location along the longitudinal direction of the pump tube 41 to thereby squeeze out the liquid within the pump tubes 41. However, the configuration of the blood purification device 100 is not limited to this example, and a squeezing roller pump may be employed. In this configuration, the tube pressing element of the pump unit is a rotor, and the pump tubes 41 having an arc portion along the outer periphery of the rotor are pressed by a stator serving as a tube receiver having an arc portion along the outer periphery of the pump tube 41. In the configuration using a roller pump, the stator, the rotor, and the pump tubes are assembled to the cassette 30, and the driver unit is attached to the device body 10, and the cassette 30 may be attachable and detachable with respect to the device body 10 such that, when the cassette 30 is assembled to the device body 10, the rotor engages the driver units and, when the cassette 30 is removed from the device body 10, the rotor is detached from the driver units.

Further, in the configuration that employs a squeezing roller pump, the pump tube 41 including an arc portion along the outer periphery of the rotor and the stator including an arc portion along the outer periphery of the pump tube 41 are assembled to the casing 31 of the cassette 30, and the rotor and the driver unit are attached to the device body 10. The cassette 30 may be assembled to the device body 10 such that the pump tube 41 is disposed between the rotor and the stator.

The blood purification device 100 according to this embodiment further enables measurement of only the load of the removed water container 37 housed within the cassette 30 with the load detector 21 mounted on the device body 10, not on the disposable cassette 30, when the cassette 30 is assembled to the housing 11 of the device body 10. This further simplifies handling of the blood purification device 100.

While in the description of the blood purification device 100 according to this embodiment, the cassette 30 is assembled to the device body 10 with the fitting 18, the cassette 30 may be assembled to the device body 10 with a fastening component or by rotating a lever, for example. Further, while in the above description, the cassette 30 includes the blood inlet nozzle 51a and the blood outlet nozzle 51b, the blood purification device 100 is not limited to this configuration and may be configured such that part of the tubes of the blood loop directed to the patient's body extend out from the cassette 30.

Figure 6:
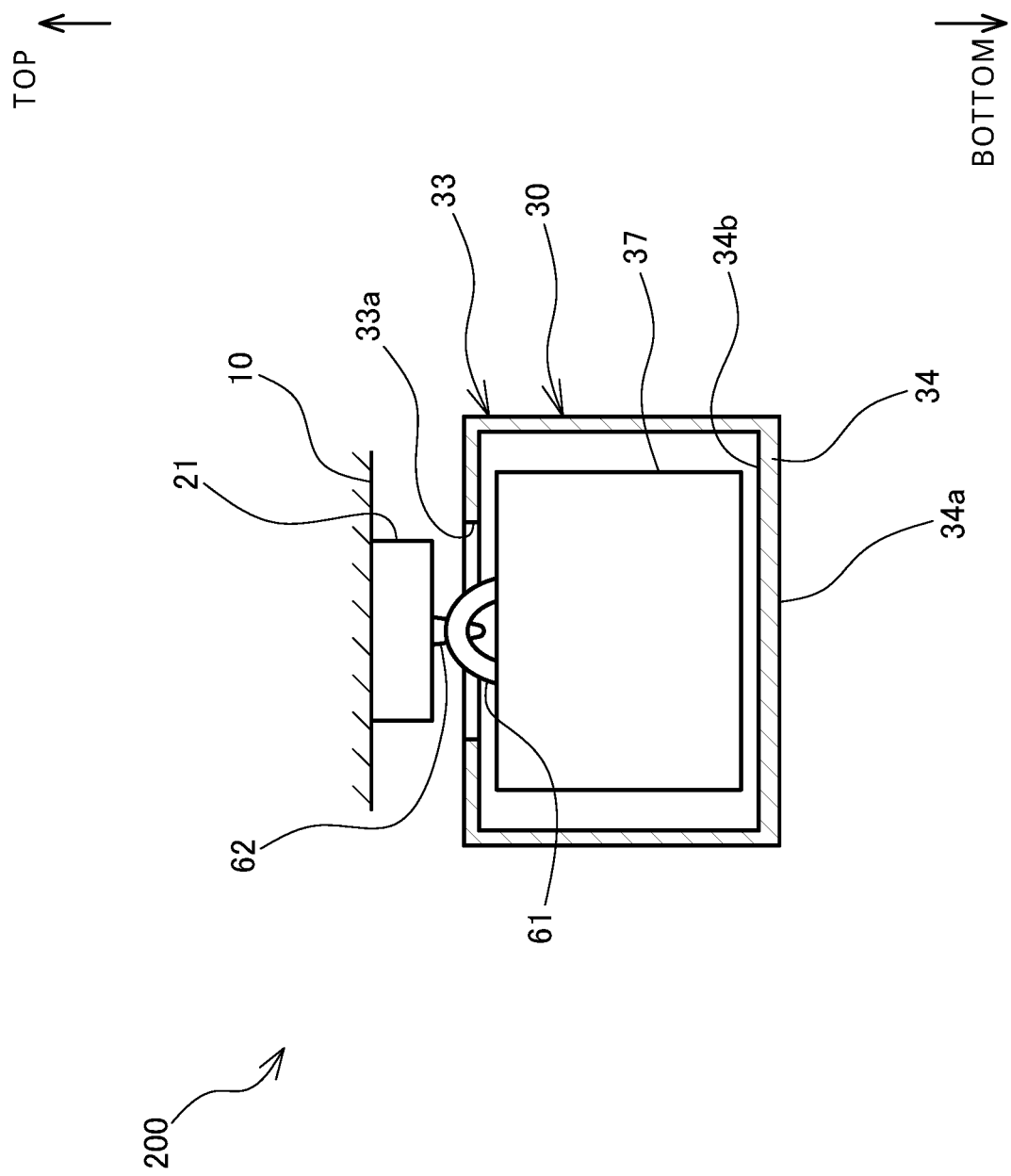
FIG. 6 is an explanatory view illustrating a load transmission mechanism of a blood purification device according to another embodiment.
Figure 7:
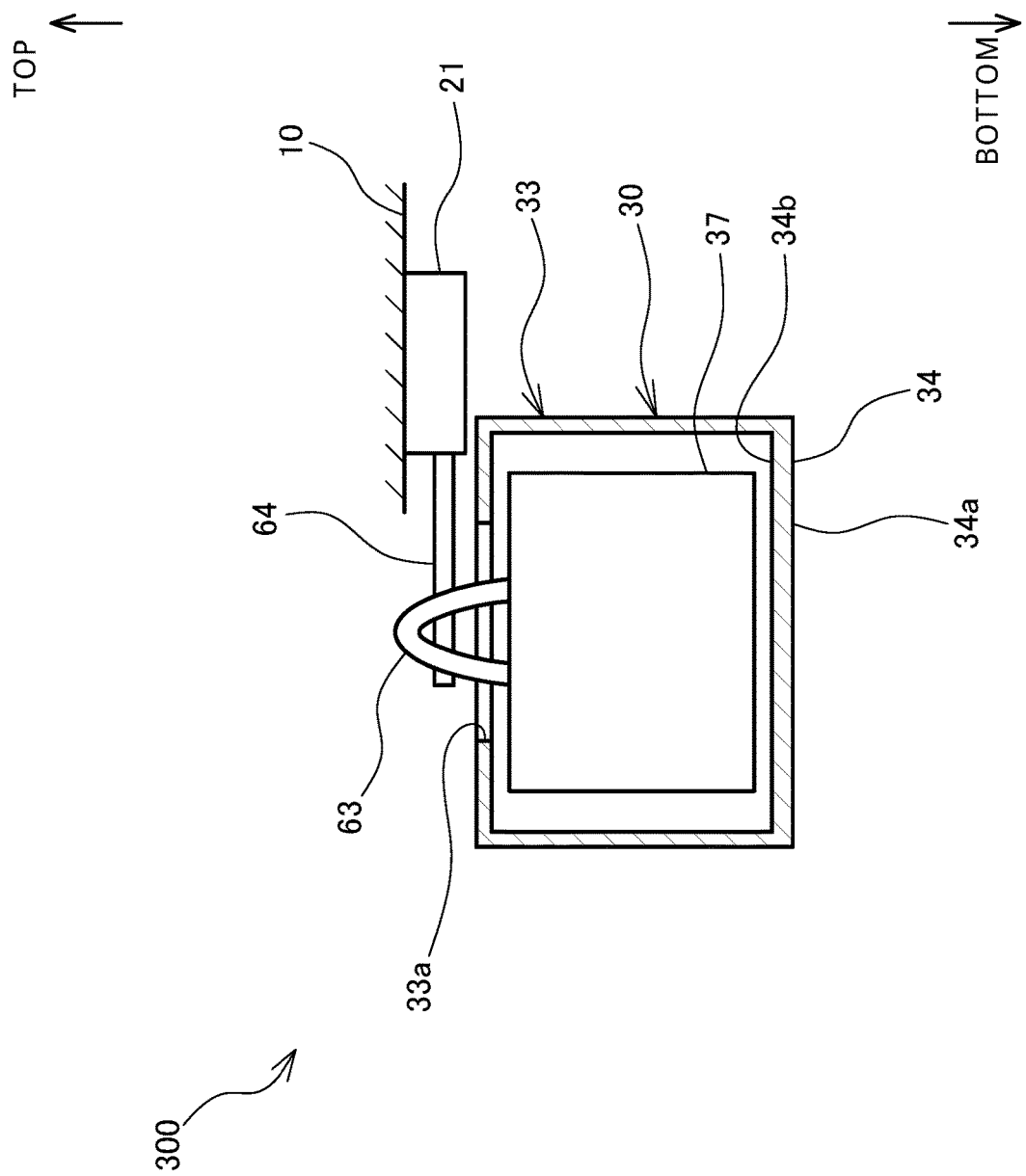
FIG. 7 is an explanatory view illustrating a load transmission mechanism of a blood purification device according to another embodiment.

Referring to FIGS. 6 and 7, blood purification devices 200 and 300 according to further embodiments will be described. Further description of the elements similar to those of the blood purification device 100 described above by reference to FIGS. 1 to 5 is omitted.

In a blood purification device 200 illustrated in FIG. 6, the cassette 30 has an opening 33a, in a portion on a top board of a front cover 33 that houses the removed water container 37; the removed water container 37 includes, on the upper part, a handle 61 serving as a protruding engaging unit; and a hook 62 that is a connector is coupled with the load detector 21 mounted on the housing 11 of the device body 10. When the cassette 30 is assembled to the housing 11 of the device body 10, the hook 62 engages the handle 61 to allow the removed water container 37 to be suspended from the load detector 21, such that the bottom face 37a of the removed water container 37 is lifted up off the upper face 34b of the bottom board 34 of the cassette 30. This results in transmission of the load of the removed water container 37 to the load detector 21 mounted on the device body 10 to thereby enable measurement of the load of the removed water container 37 with the load detector 21.

In the blood purification device 200 according to this embodiment, the opening 33a of the front cover 33, the handle 61, and the hook 62 form a load transmission mechanism that transmits the load of the removed water container 37 to the load detector 21.

In a blood purification device 300 illustrated in FIG. 7, the handle 61 of the blood purification device 200 is modified into a protruding handle 63 that protrudes upward through the opening 33a, and the hook 62 is modified as an arm 64. When the cassette 30 is assembled to the housing 11 of the device body 10, the arm 64 engages the protruding handle 63 that protrudes through the top board of the front cover 33 of the cassette 30 to thereby lift the removed water container 37 up off the upper face 34b of the bottom board 34 of the cassette 30. The protruding handle 63 and the arm 64 then transmit the load of the removed water container 37 to the load detector 21 mounted on the device body 10 for measuring the load of the removed water container 37 with the load detector 21.

In the blood purification device 300 according to this embodiment, the opening 33a of the front cover 33, the protruding handle 63, and the arm 64 form a load transmission mechanism that transmits the load of the removed water container 37 to the load detector 21.

The blood purification devices 200 and 300 described above achieve advantages similar to the advantages of the blood purification device 100.

Figure 8:
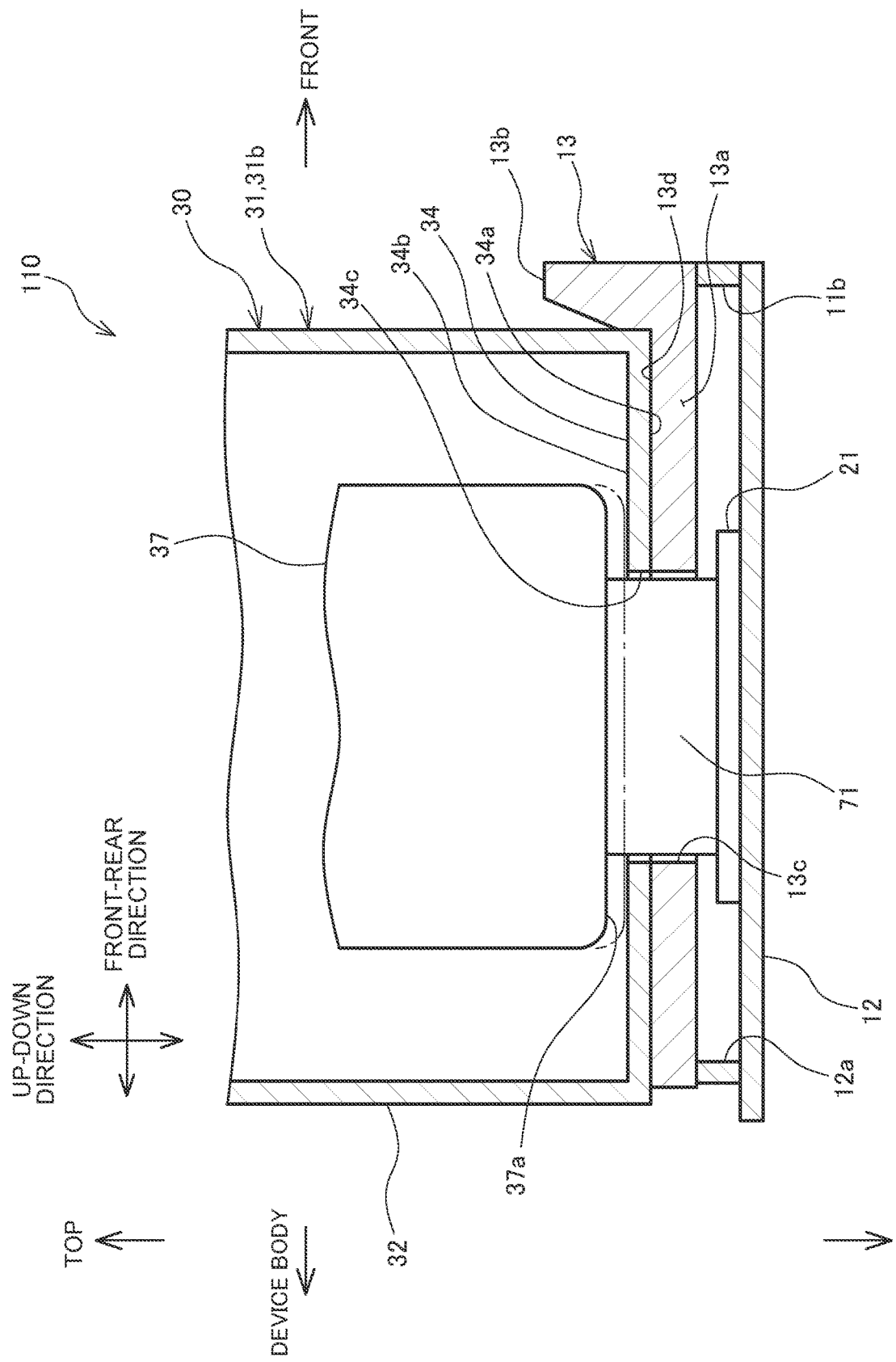
FIG. 8 is a cross section illustrating a load transmission mechanism in a modification example of the blood purification device illustrated in FIG. 1.

Referring now to FIG. 8, a blood purification device 110 which is a modification example of the blood purification device 100 described above by reference to FIGS. 1 to 5 will be described. The blood purification device 110 illustrated in FIG. 8 includes a heater 71 in place of the spacer 22 of the blood purification device 100 described by reference to FIGS. 1 to 5, which is positioned in a region under the removed water container 37 housed in the cassette 30 when the cassette 30 is assembled to the device body 10. The heater 71 is configured to be partially inserted, from below, into the cassette 30 when the cassette 30 is assembled to the device body 10. The remaining configuration is the same as that of the blood purification device 100.

As illustrated in FIG. 8, the heater 71 has such a thickness that allows the heater 71 to protrude from the upper face 34b of the bottom board 34 of the cassette 30, when the cassette 30 is assembled to the device body 10 to make the undersurface 34a of the bottom board 34 in contact with the upper face 13d of the cassette seat 13, to thereby lift the bottom face 37a of the removed water container 37 up off the upper face 34b of the bottom board 34.

When the cassette 30 is assembled to the housing 11 of the device body 10 to bring the undersurface 34a of the bottom board 34 into contact with the upper face 13d of the cassette seat 13, the upper face of the heater 71 protrudes from the upper face 34b of the bottom board 34 to lift the bottom face 37a of the removed water container 37 up off the upper face 34b of the bottom board 34. The heater 71 is thus sandwiched between the load detector 21 and the bottom face 37a of the removed water container 37 to thereby transmit the load of the removed water container 37 to the load detector 21. The removed water container 37 is thus placed above the load detector 21 to allow the load detector 21 mounted on the device body 10 to measure the load of the removed water container 37 housed in the cassette 30.

The heater 71 comes into contact with the bottom face 37a of the removed water container 37 to heat the liquid stored in the removed water container 37, and may be a sheet or plate shaped heater plate, for example. The heater 71 may also be an electromagnetic heater that heats a metal plate attached to the bottom face 37a of the removed water container 37 with high frequency electromagnetic force or a high-frequency induction heater. Heating the liquid stored in the removed water container 37 with the heater 71 enables heating of the dialysate to maintain the temperature of the blood reinfused to the patient.

Figure 9:
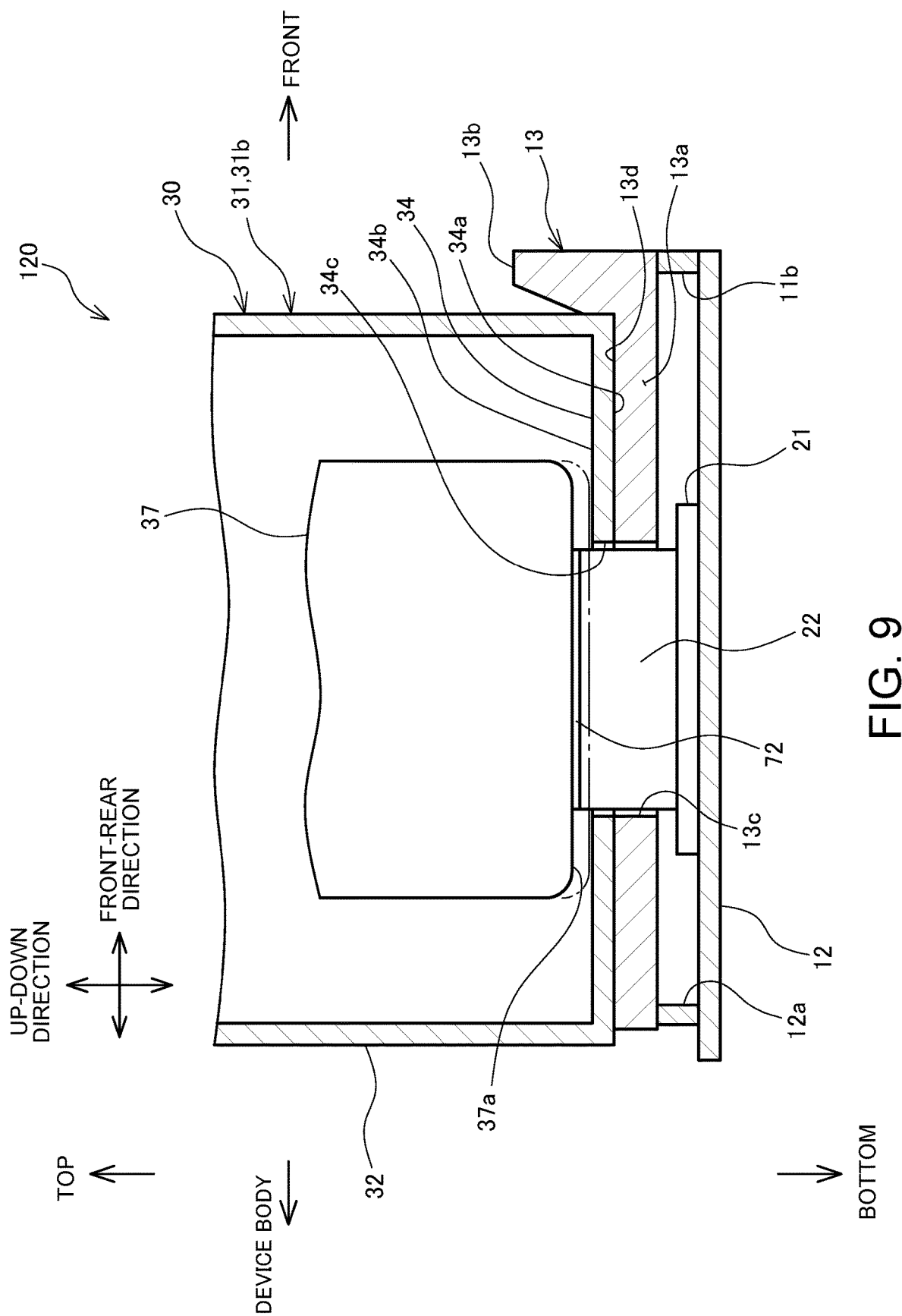
FIG. 9 is a cross section illustrating another modification example of the blood purification device illustrated in FIG. 1.

Referring now to FIG. 9, a blood purification device 120 which is another modification example of the blood purification device 100 will be described. The blood purification device 120 illustrated in FIG. 9 includes a heater 72 having a thin sheet or plate shape on the spacer 22 positioned in a region under the removed water container 37 of the blood purification device 100 described by reference to FIGS. 1 to 5. The heater 72 is configured to be entirely housed within the cassette 30 when the cassette 30 is assembled to the device body 10. The remaining configuration is the same as that of the blood purification device 100.

As illustrated in FIG. 9, the spacer 22 has such a thickness that allows the spacer 22 to protrude from the upper face 34b of the bottom board 34 of the cassette 30, when the cassette 30 is assembled to the device body 10 to bring the bottom face 34a of the bottom board 34 into contact with the upper face 13d of the cassette seat 13. The heater 72 disposed on the spacer 22 may be a heater plate having a thin sheet or plate shape, or may include a Peltier element, for example.

When the cassette 30 is assembled to the housing 11 of the device body 10 to bring the undersurface 34a of the bottom board 34 into contact with the upper face 13d of the cassette seat 13, the heater 72, along with the spacer 22, is sandwiched between the load detector 21 and the bottom face 37a of the removed water container 37 to thereby transmit the load of the removed water container 37 to the load detector 21. In this manner, the load detector 21 mounted on the device body 10 may measure the load of the removed water container 37 housed in the cassette 30. Further, similar to the blood purification device 110 described above, heating the liquid stored in the removed water container 37 with the heater 72 enables heating of the dialysate to maintain the temperature of the blood to be reinfused to the patient.

The heater 72 may have any thickness that allows the total thickness of the spacer 22 and the heater 72 to protrude from the upper face 34b of the bottom board 34 when the undersurface 34a of the bottom board 34 of the cassette 30 is in contact with the upper face 13d of the cassette seat 13, and may be greater than that illustrated in FIG. 9 such that the heater 72 enters the hole 34c. In this configuration, the heater 72 partially enters the cassette 30 when the cassette 30 is assembled to the device body 10.

Figure 10:
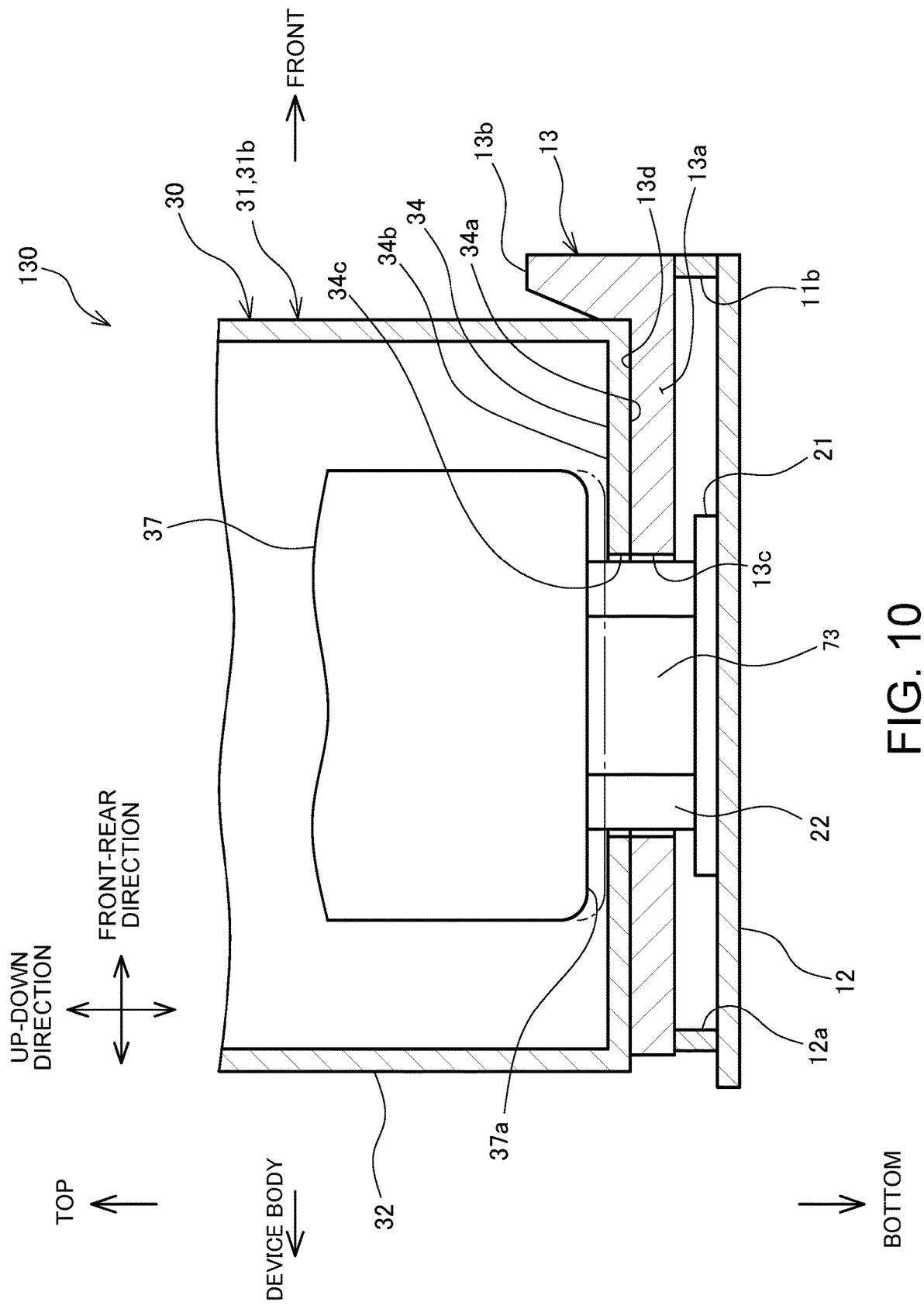
FIG. 10 is a cross section illustrating still another modification example of the blood purification device illustrated in FIG. 1.

Referring now to FIG. 10, a blood purification device 130 will be described. The blood purification device 130 illustrated in FIG. 10 includes the spacer 22 of the blood purification device 100 described above by reference to FIGS. 1 to 5 but having an annular shape, and a heater 73 disposed inside the spacer 22. The heater 73 is positioned in a region under the removed water container 37 housed in the cassette 30 that is assembled to the device body 10. An upper part of the heater 73 enters the cassette 30 through the hole 34c when the cassette 30 is assembled to the device body 10. The heater 73 may have a height that is level with the upper face of the spacer 22 to thereby receive the load of the removed water container 37 and transmit the load to the load detector 21, or a height that is lower than the upper face of the spacer 22 to thereby prevent receiving of the load of the removed water container 37. The heater 73 need not pass through the hole 34c; in this configuration, the heater 73 does not enter the cassette 30, and is positioned near a region under the cassette 30. The remaining configuration is the same as that of the blood purification device 100.

The annular spacer 22, similar to the spacer 22 of the blood purification device 100 described above, is sandwiched between the removed water container 37 and the load detector 21 to transmit the load of the removed water container 37 to the load detector 21. Heating the liquid stored in the removed water container 37 with the heater 73 enables heating of the dialysate to maintain the temperature of the blood reinfused to the patient.

Figure 11:
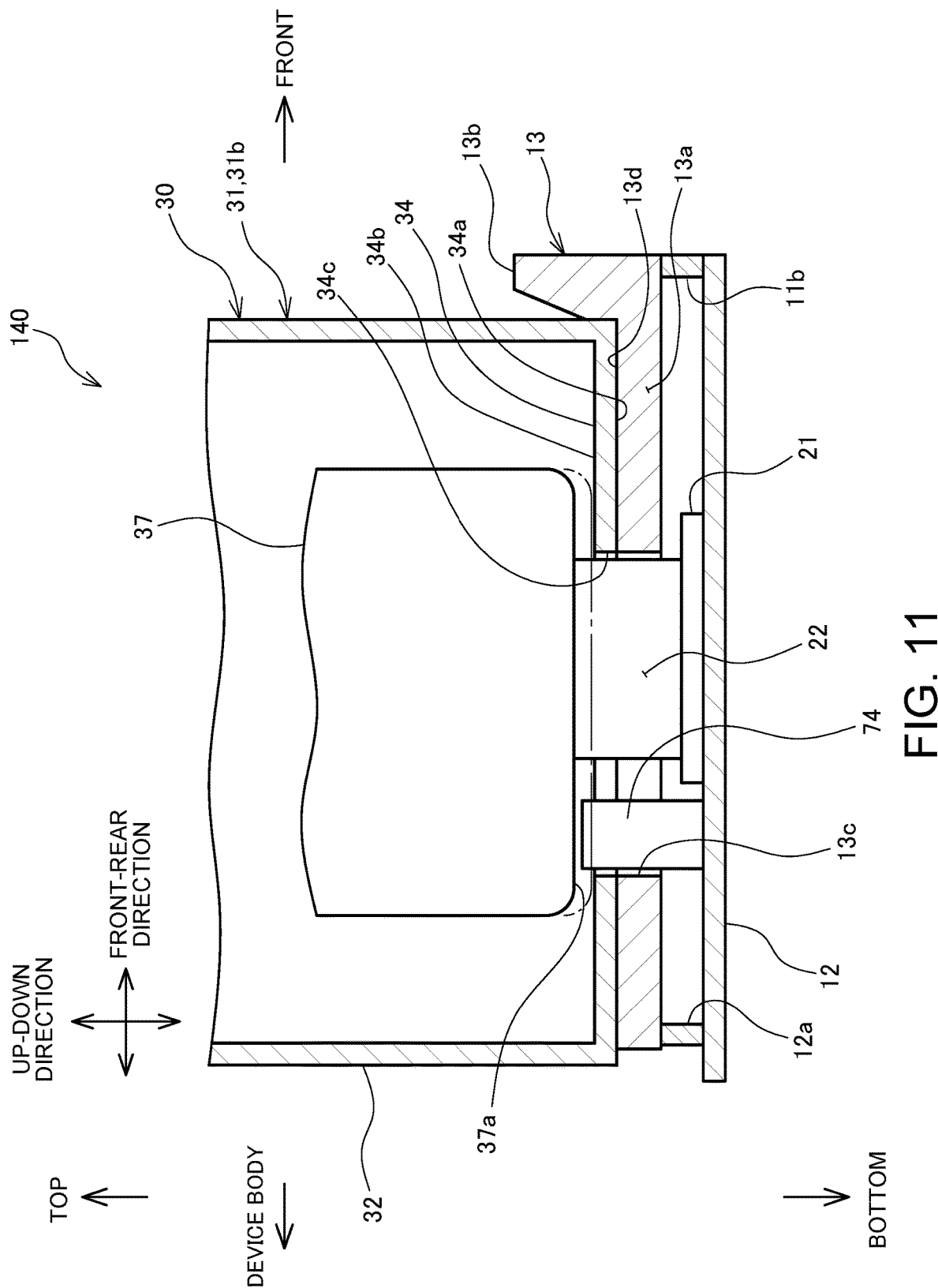
FIG. 11 is a cross section illustrating still another modification example of the blood purification device illustrated in FIG. 1.

Referring now to FIG. 11, a blood purification device 140, which is another modification example of the blood purification device 100, will be described. As illustrated in FIG. 11, the blood purification device 140 includes a heater 74, independently of the spacer 22 and load detector 21, on the base 12 under the opening 13c formed in the cassette seat 13. The heater 74 is positioned under the bottom face 37a of the removed water container 37 when the cassette 30 is assembled to the device body 10. While an upper part of the heater 74 enters, through the hole 34c, the cassette 30 when the cassette 30 is assembled to the device body 10, the heater 74 is configured to have a height that is lower than the upper face of the spacer 22, in order to prevent receiving of the load of the removed water container 37. The heater 74 need not pass through the hole 34c; in this configuration, the heater 74 does not enter the cassette 30, and is positioned near a region under the cassette 30. The heater 74 may be an electromagnetic heater or a high frequency induction heater, for example. The heater 74 may include a heater plate having a sheet or plate shape, or a Peltier element, for example, and may be mounted on the base 12 under the opening 13c. The heater 74 may be disposed in any region under the removed water container 37 housed in the cassette 30 assembled to the device body 10, and may be mounted on the base 12 under the receiving plate 13a of the cassette seat 13 in the periphery of the opening 13c, rather than in the region under the opening 13c.

The blood purification device 140, similar to the blood purification device 110, heats the liquid stored in the removed water container 37 with the heater 74 to thereby heat the dialysate and maintain the temperature of the blood reinfused to the patient.

Figure 12:
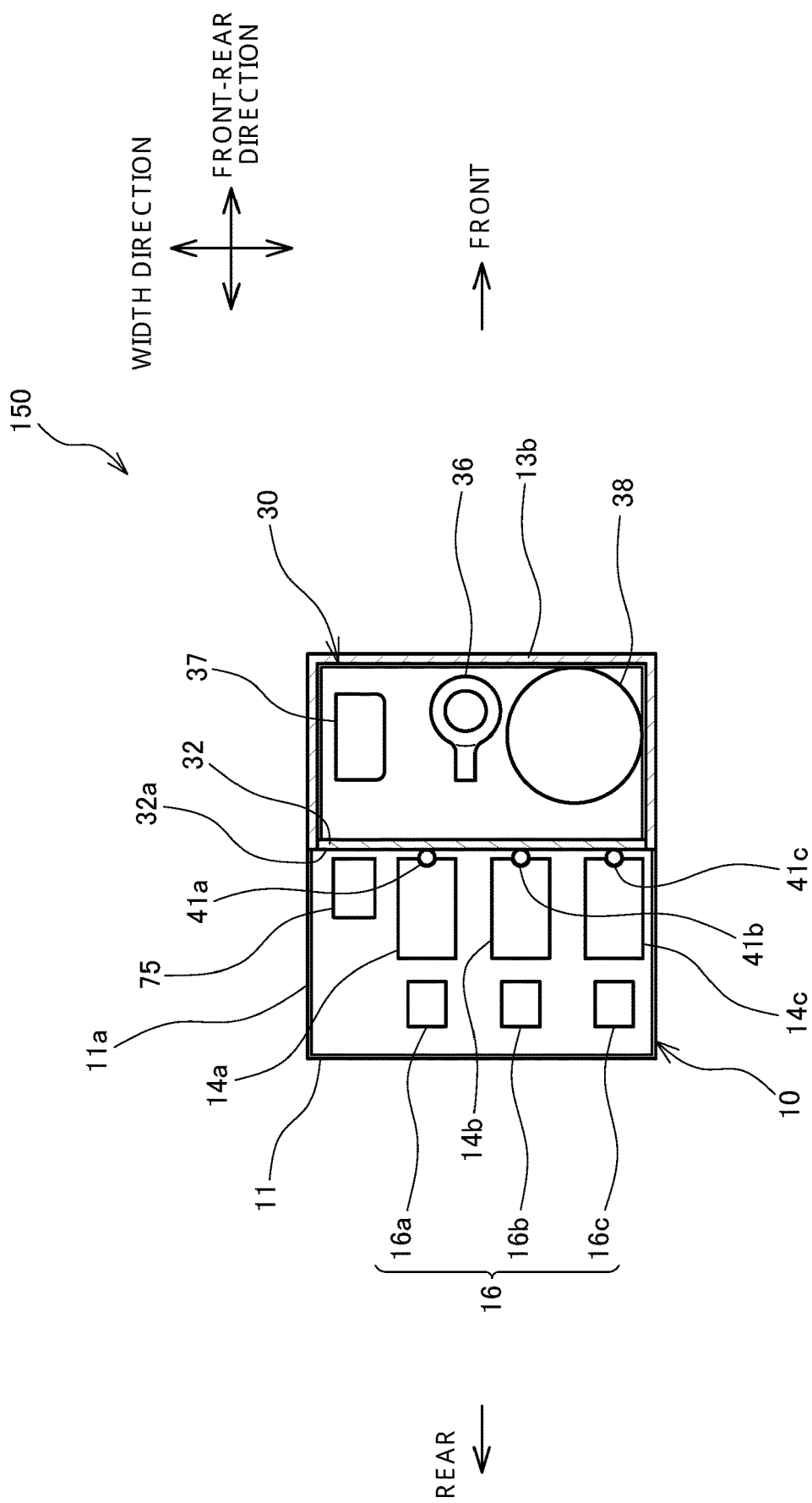
FIG. 12 is a horizontal cross section illustrating another modification example of the blood purification device illustrated in FIG. 1.

Referring now to FIG. 12, a blood purification device 150 that is another example of the blood purification device 100 described above will be described. The blood purification device 150 illustrated in FIG. 12 includes a heater 75 positioned near a side face of the cassette 30 when the cassette 30 of the device body 10 is assembled to the device body 10. The remaining configuration is the same as that of the blood purification device 100.

As illustrated in FIG. 12, the blood purification device 150 includes the finger casings 14a to 14c in a region toward the dialysate regeneration column 38 to thereby form a space between the finger casing 14a and the side board 11a of the housing 11 of the device body 10, and includes the heater 75 in this space. When the cassette 30 is assembled to the device body 10, the heater 75 is positioned opposite the removed water container 37 housed in the cassette 30 in the front-rear direction, with the rear board 32 of the cassette 30 being interposed between the heater 75 and the removed water container 37.

The heater 75 is a non-contact heater, which heats the removed water container 37 or the liquid stored in the removed water container 37 in a non-contact manner via the rear board 32 of the cassette 30. The heater 75 may be, for example, an electromagnetic heater, or an optical heater that illuminates the removed water container 37 with light through a slit formed in the rear board 32 to thereby heat the removed water container 37. The blood purification device 150, similar to the blood purification devices 110, 120, and 130, heats the liquid stored in the removed water container 37 with the heater 75 to thereby heat the dialysate and maintain the temperature of the blood reinfused to the patient.

Figure 13:
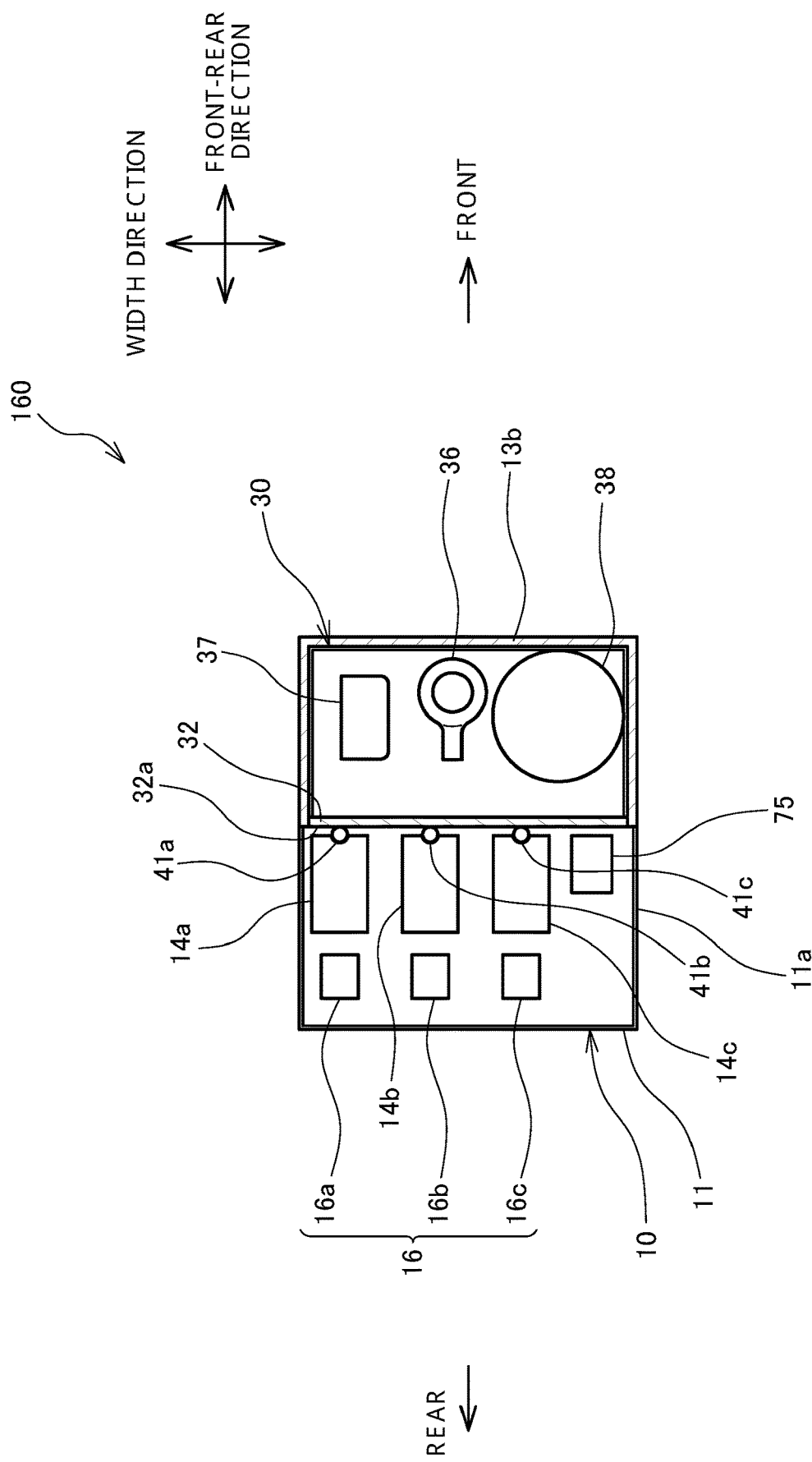
FIG. 13 is a horizontal cross section illustrating still another modification example of the blood purification device illustrated in FIG. 1.

A blood purification device 160 illustrated in FIG. 13, contrary to the blood purification device 150 described above by reference to FIG. 12, includes the heater 75 that is located opposite the dialysate regeneration column 38 housed in the cassette 30 in the front-rear direction, via the rear board 32 of the cassette 30, when the cassette 30 is assembled to the device body 10. The remaining configuration is the same as that of the blood purification device 150 described above by reference to FIG. 12.

The blood purification device 160 heats the liquid stored in the dialysate regeneration column 38 with the heater 75 to thereby heat the dialysate and maintain the temperature of the blood reinfused to the patient.

Figure 14:
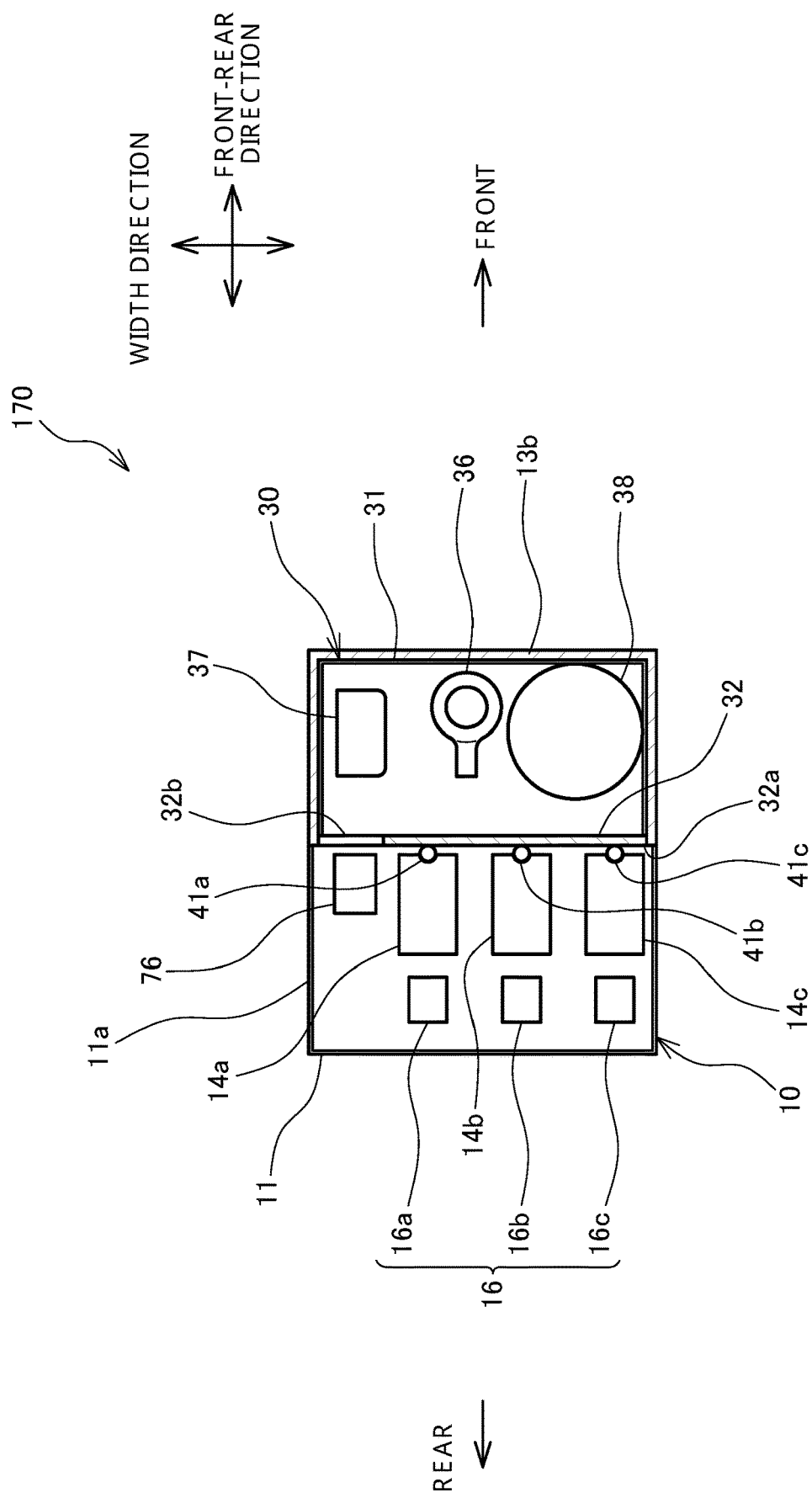
FIG. 14 is a horizontal cross section illustrating still another modification example of the blood purification device illustrated in FIG. 1.

A blood purification device 170 illustrated in FIG. 14 includes an opening 32b in the casing 31 of the cassette 30 of the blood purification device 150 described by reference to FIG. 12 on the rear board 32 located adjacent to the device body 10 and includes a warm air generator 76 in the device body 10 opposite ??the removed water container 37?? via the opening 32b in the front-rear direction.

The blood purification device 170 enables flowing of warm air from the warm air generator 76 through the opening 32b into the casing 31 of the cassette 30 to warm the dialyzer 36, the removed water container 37, and the dialysate regeneration column 38 housed in the cassette 30, thereby heating the dialysate and maintaining the temperature of the blood reinfused to the patient.

Figure 15:
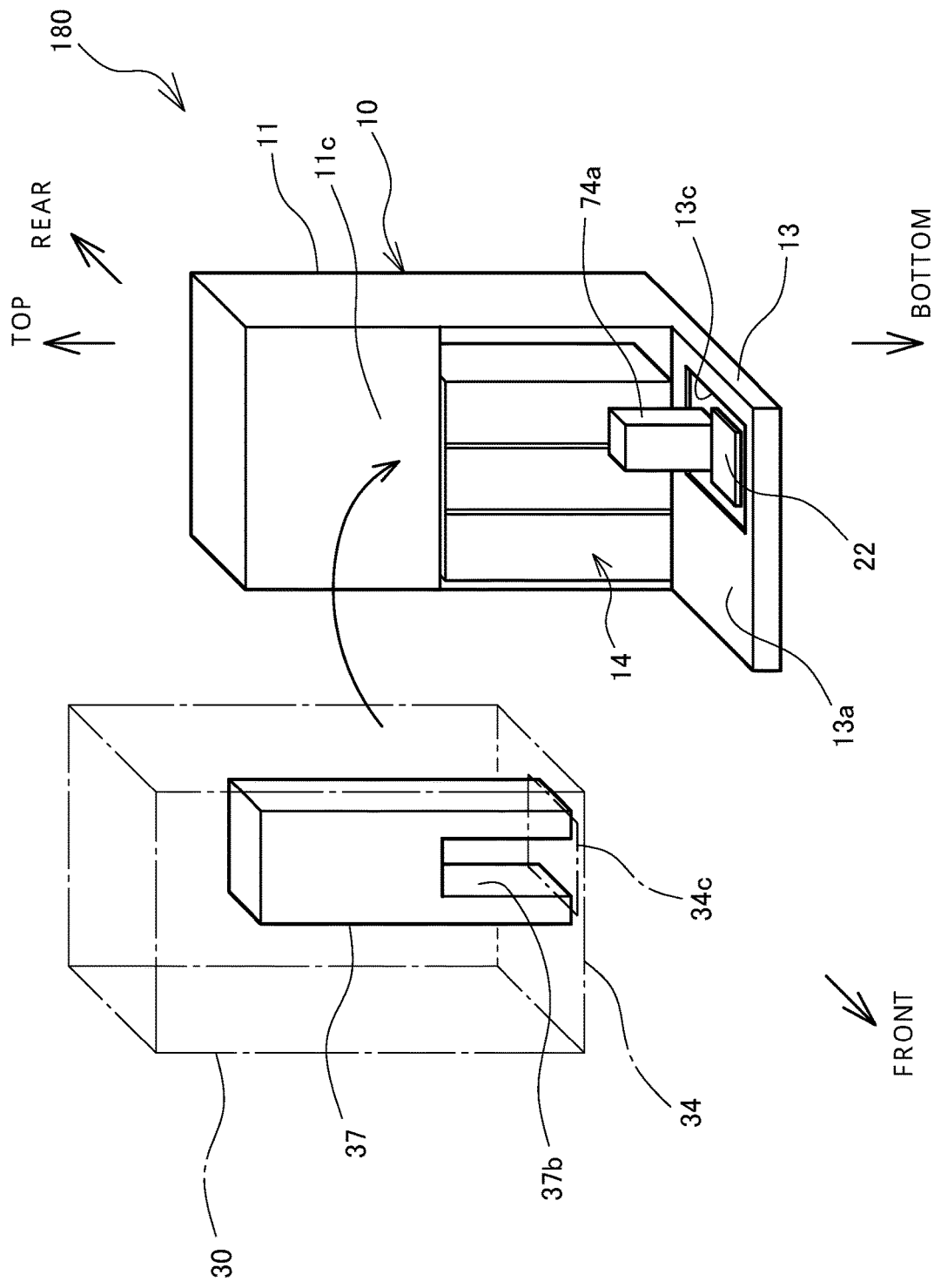
FIG. 15 is an exploded perspective view illustrating another modification example of the blood purification device illustrated in FIG. 1.

A blood purification device 180 illustrated in FIG. 15 includes the removed water container 37 having, on the bottom, a recess portion 37b which is configured to receive a heater 74a when the cassette 30 is assembled to the device body 10.

Figure 16:
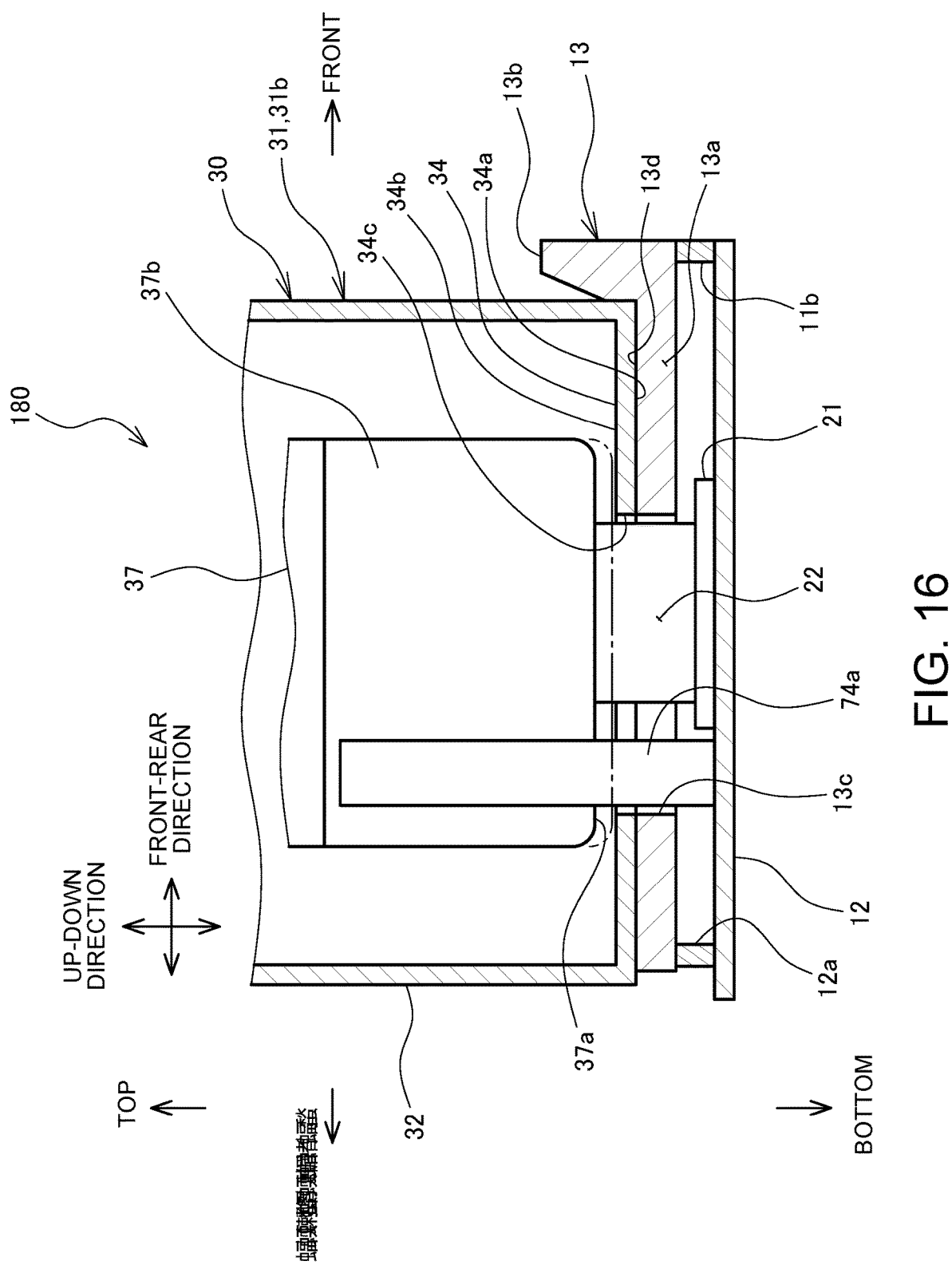
FIG. 16 is a cross section of another modification example of the blood purification device illustrated in FIG. 15.

In the blood purification device 180, the heater 74a has a greater height than the heater 74 of the blood purification device 140 described by reference to FIG. 11, and the removed water container 37 includes the recess portion 37b on the bottom. When the cassette 30 is assembled to the receiving plate 13a of the cassette seat 13 of the device body 10, the heater 74a enters the interior of the cassette 30 and also enters the recess portion 37b from under the removed water container 37 housed in the cassette 30, as illustrated in FIG. 16. The bottom face 37a of the removed water container 37 abuts against the upper face of the spacer 22, such that the load of the removed water container 37 is detected by the load detector 21. Here, the heater 74a has a height which does not contact the upper part of the recess portion 37b, to thereby avoid transmission of the load of the removed water container 37.

The blood purification device 180 heats the removed water container 37 more efficiently with the heater 74a inserted in the recess portion 37b of the removed water container 37. While in the embodiment described above, the heater 74a enters the interior of the cassette 30 from under the cassette 30, other configurations may also be employed. In one example, the cassette 30 has an opening on the rear board 32 and the heater 74a is disposed on a partition board 11c of the device body 10, such that, in assembling the cassette 30 to the device body 10, the heater 74a may be inserted laterally from the back of the cassette 30. In another example, the heater 74a is disposed in the upper part of the device body 10 while the cassette 30 has an opening on the top board, such that in assembling the cassette 30 to the device body 10, the heater 74a may be inserted into the cassette 30 from above the cassette 30.

Figure 17:
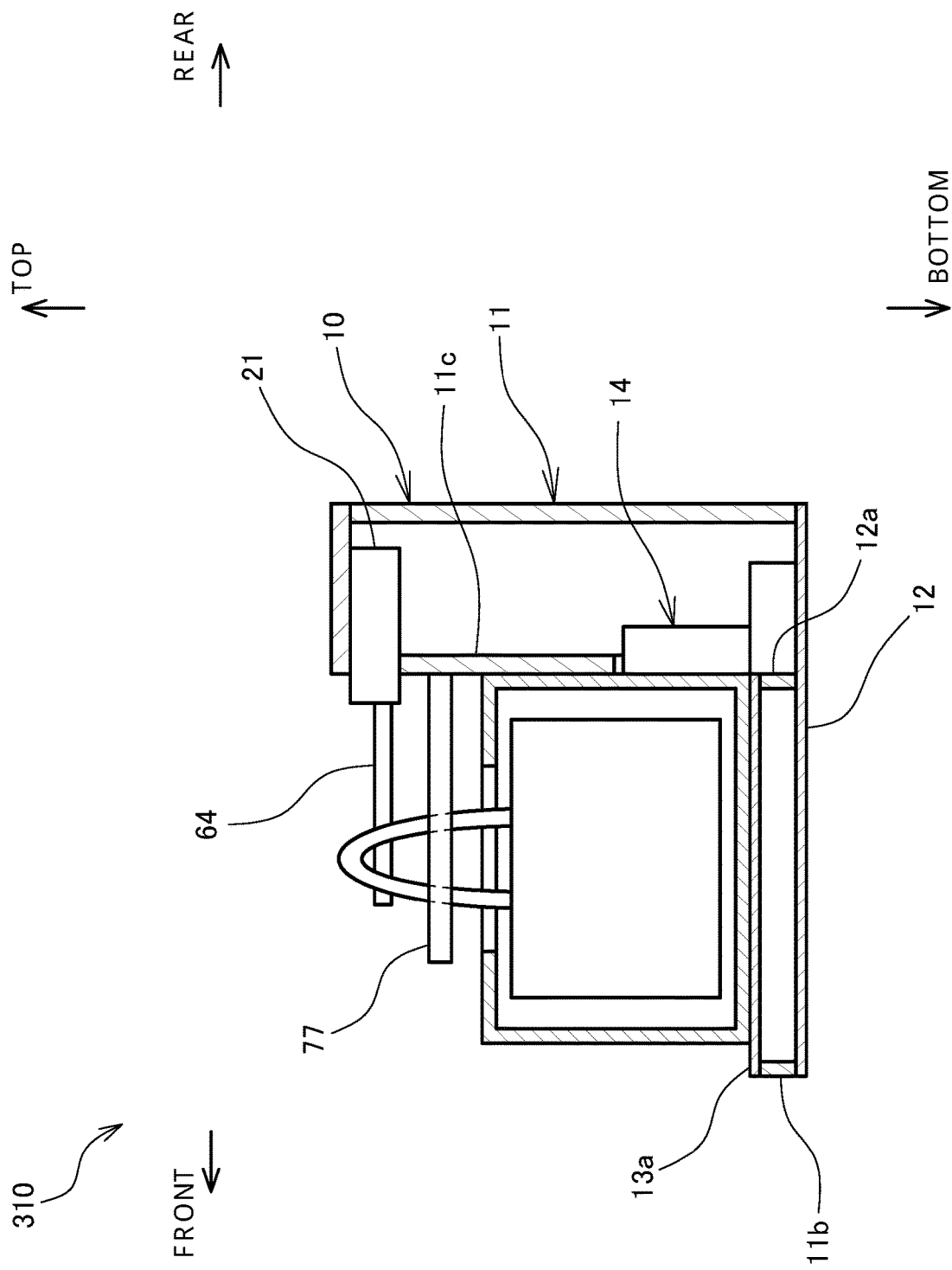
FIG. 17 is a cross section of a modification example of the blood purification device illustrated in FIG. 7.

A blood purification device 310 illustrated in FIG. 17 includes a heater 77 protruding at a location above the cassette 30 from the partition board 11c of the housing 11 of the device body 10 adjacent to the cassette 30, in a configuration including the removed water container 37 that is suspended from the arm 64 of the load detector 21 when the cassette 30 is assembled to the device body 10, as in the blood purification device 300 described above by reference to FIG. 7. The heater 77 is disposed to be located near a region above the cassette 30, when the cassette 30 is assembled to the device body 10.

Figure 18:
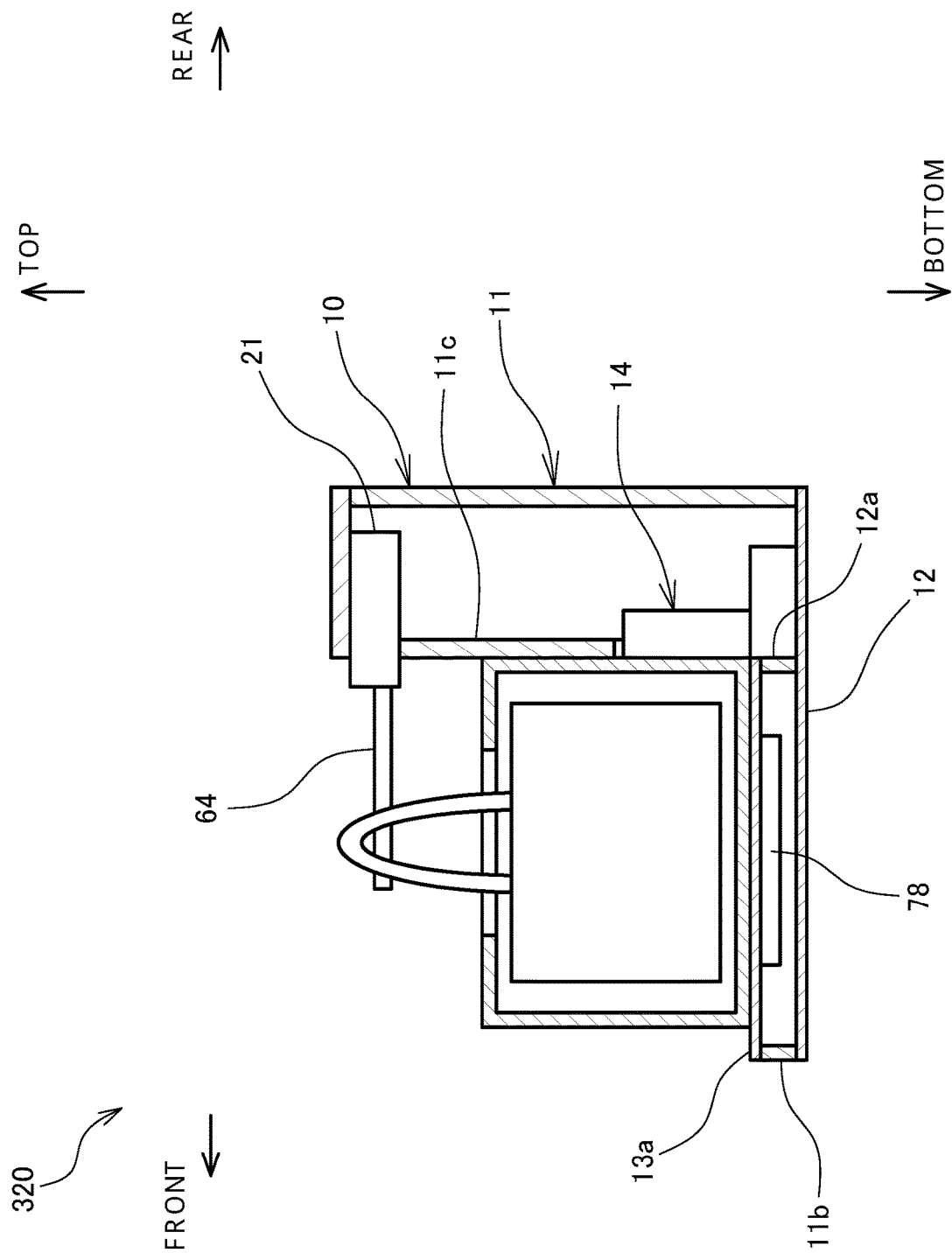
FIG. 18 is a cross section of another modification example of the blood purification device illustrated in FIG. 7.

A blood purification device 320 illustrated in FIG. 18 includes a heater 78 disposed on the undersurface of the receiving board 13a of the cassette seat 13 such that the heater 78 is located in a region under the cassette 30 when the cassette 30 is assembled to the device body 10.

Figure 19:
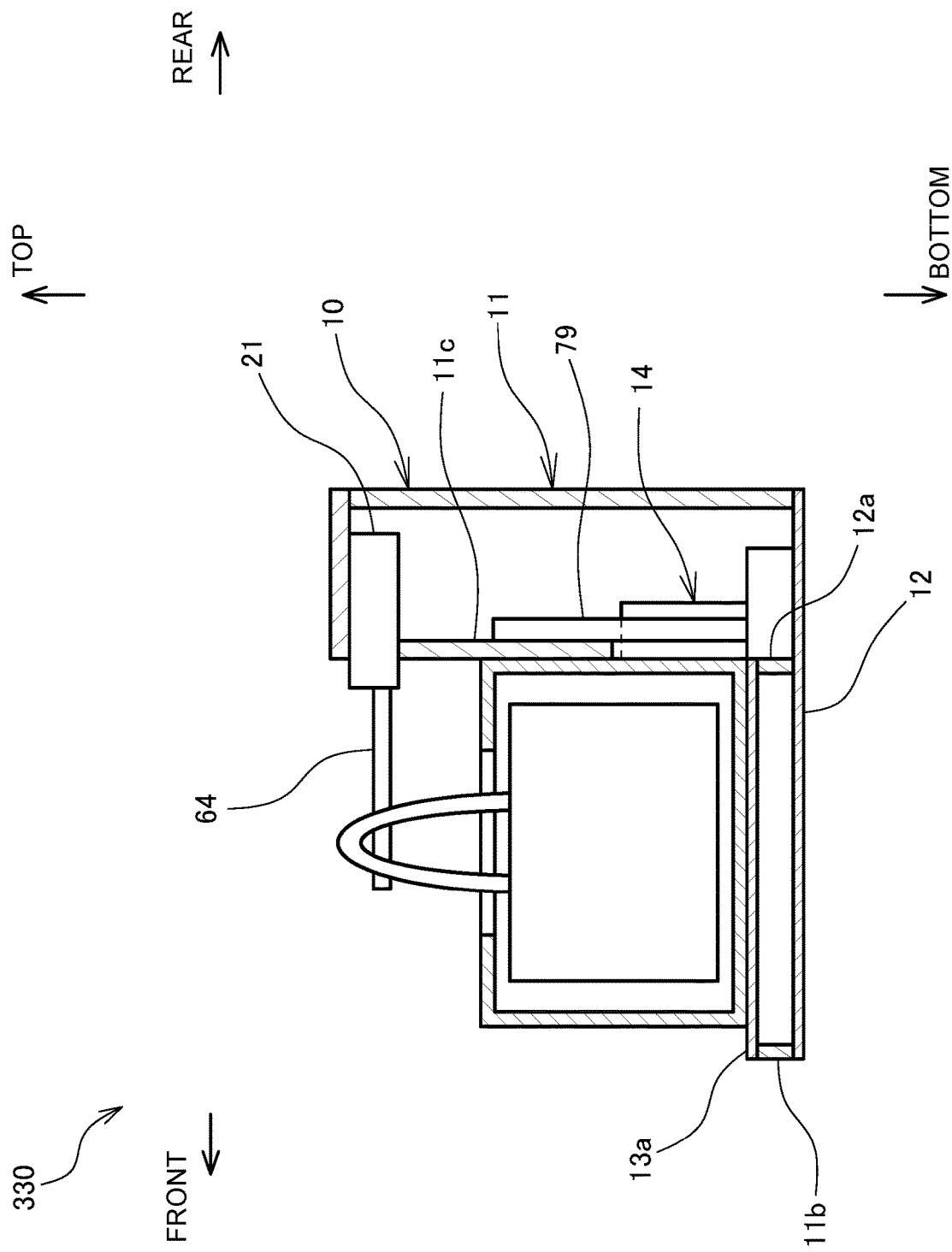
FIG. 19 is a cross section of still another modification example of the blood purification device illustrated in FIG. 7.

A blood purification device 330 illustrated in FIG. 19 includes a heater 79 in the housing 11 of the device body 10 on the partition board 11c adjacent to the cassette 30. The heater 79 is disposed to be located near the side face of the cassette 30 when the cassette 30 is assembled to the device body 10.

The blood purification devices 310, 320, and 330 described by reference to FIG. 17 to FIG. 18 heat the dialyzer 36, the removed water container 37, and the dialysate regeneration column 38 housed in the cassette 30 with the heaters 77, 78, and 79, to thereby enable heating of the dialysate and maintaining of the blood reinfused in the patient.

The present invention is not limited to the embodiments described above and includes all of modifications and corrections that do not depart from the technical range or gist of the invention as defined in the claims.

REFERENCE SIGNS LIST

10 device body, 11 housing, 11a side board, 11b front board, 11c partition board, 12 base, 12a rib, 13 cassette seat, 13a receiving board, 13b vertical flange, 13c, 33a opening, 13d, 34b upper face, 14, 14a to 14c finger casing, 15,15a to 15c finger, 16, 16a to 16c driver unit, 18 fitting, 20 controller, 21 load detector, 22 spacer, 30 cassette, 31 casing, 31a side board, 31b front board, 32 rear board, 32a outer face, 32b opening, 34 bottom board, 34a undersurface, 34c hole, 35 hook, 36 dialyzer, 37 removed water container, 37a bottom face, 38 dialysate regeneration column, 41, 41a to 41c pump tube, 51a blood inlet nozzle, 51b blood outlet nozzle, 61 handle, 62 hook, 63 protrusion handle, 64 arm, 71 to 74, 74a, 75, 77 to 79 heater, 76 warm air generator, 100, 110, 120, 130, 140, 150, 160, 180, 200, 300, 310, 320, 330 blood purification device.

The invention claimed is:

1. A blood purification device comprising:
   a device body; and
   a cassette including a casing that houses a removed water container, the cassette to be removably assembled to the device body, wherein
   a load detector is mounted on the device body, the load detector being configured to measure a load of the removed water container,
   the blood purification device further comprises a load transmission mechanism configured to transmit to the load detector the load of the removed water container housed in the cassette, the load transmission mechanism including a hole in a bottom board of the cassette in a portion where the removed water container is housed, and
   the removed water container is configured to be placed on or above the load detector.

2. The blood purification device according to claim 1, wherein
   the device body includes a base on which the load detector is mounted, and
   the load detector is inserted through the hole.

3. The blood purification device according to claim 2, wherein
   the device body includes a cassette seat configured to receive the cassette,
   the load transmission mechanism includes the hole, and an opening in the cassette seat at a location corresponding to the hole in the cassette, and
   the load detector is inserted through the hole and the opening.

4. The blood purification device according to claim 1, wherein
   the device body comprises a base on which the load detector is mounted,
   the load transmission mechanism comprises the hole, and a spacer to be inserted through the hole, the spacer being sandwiched between the load detector mounted on the base and a bottom face of the removed water container to thereby lift the removed water container up off a bottom board of the cassette, and
   the removed water container is configured to be placed on the spacer on top of the load detector.

5. The blood purification device according to claim 4, wherein
   the device body comprises a cassette seat configured to receive the cassette, the cassette seat being disposed with an interval from the base,
   the load transmission mechanism further comprises an opening in the cassette seat at a location corresponding to the hole of the cassette, and
   the spacer is inserted through the hole and the opening and sandwiched between the load detector mounted on the base and a bottom face of the removed water container to thereby lift the removed water container up off the bottom board of the cassette that is assembled to the device body to thereby bring the bottom face of the cassette into contact with the cassette seat of the device body.

6. The blood purification device according to claim 1, wherein the device body includes a heater to be disposed such that part or all of the heater enters the interior of the cassette that is assembled to the device body.

7. The blood purification device according to claim 1, wherein
the device body includes a heater to be disposed near the cassette that is assembled to the device body.

8. A blood purification device comprising:
a device body; and
a cassette including a casing that houses a removed water container, the cassette to be removably assembled to the device body, wherein
a load detector is mounted on the device body, the load detector being configured to measure a load of the removed water container,
the blood purification device further comprises a load transmission mechanism configured to transmit to the load detector the load of the removed water container housed in the cassette,
the load transmission mechanism comprises:
an opening in a top board of the cassette in a portion where the removed water container is housed;
an engaging unit protruding on an upper portion of the removed water container; and
a connector coupled with the load detector mounted on the device body, the connector being configured to engage the engaging unit of the removed water container through the opening to thereby lift the removed water container up off a bottom board of the cassette assembled to the device body, and
the removed water container is suspended from the load detector via the connector.

9. A blood purification device comprising:
a device body; and
a cassette to be removably assembled to the device body, wherein
the cassette comprises a casing that further houses a removed water container, a dialyzer, and a dialysate regeneration column, the cassette being attachable and removable with respect to the device body,
the removed water container is provided separately from the casing,
the casing comprises
a hole in a bottom board in a portion where the removed water container is housed, and
an opening in a top board in a position where the removed water container is housed, and
the device body comprises a load detector configured to measure the load of the removed water container, and
the load of the removed water container is transmitted to the load detector via the hole or the opening.

10. The blood purification device according to claim 1, further comprising:
a pump unit including
an elastic pump tube;
a tube receiver configured to receive the pump tube;
a tube pressing member configured to press a portion of the pump tube onto the tube receiver: and
a driver unit configure to move the tube pressing member along a longitudinal direction of the pump tube,
the pump unit being configured to squeeze out liquid within the pump tube,
wherein
the cassette comprises at least a portion of the pump unit, and
the device body comprises a further portion of the pump unit.

11. The blood purification device according to claim 10, wherein
the cassette comprises the tube receiver and the pump tube of the pump unit,
the device body comprises the tube pressing member and the driver unit,
the tube receiver is the casing of the cassette,
the pump tube is mounted on an outer face of the casing,
the tube pressing member comprises a plurality of fingers, and
the cassette is attachable and removable with respect to the device body such that the pump tube is located between the fingers and the outer face of the casing.

12. The blood purification device according to claim 11, wherein
the cassette comprises the tube receiver, the pump tube, and the tube pressing member of the pump unit,
the device body comprises the driver unit,
the tube pressing member is a rotor,
the pump tube includes an arc portion along an outer circumference of the rotor,
the tube receiver is a stator including an arc portion along an outer circumference of the pump tube, and
the cassette is attachable and removable with respect to the device body such that the rotor engages the driver unit with the cassette being assembled to the device body and the rotor is separated from the driver unit with the cassette being removed from the device body.

13. The blood purification device according to claim 8, further comprising:
a pump unit including
an elastic pump tube;
a tube receiver configured to receive the pump tube;
a tube pressing member configured to press a portion of the pump tube onto the tube receiver: and
a driver unit configure to move the tube pressing member along a longitudinal direction of the pump tube,
the pump unit being configured to squeeze out liquid within the pump tube,
wherein
the cassette comprises at least a portion of the pump unit, and
the device body comprises a further portion of the pump unit.

14. The blood purification device according to claim 9, further comprising:
a pump unit including
an elastic pump tube;
a tube receiver configured to receive the pump tube;
a tube pressing member configured to press a portion of the pump tube onto the tube receiver: and
a driver unit configure to move the tube pressing member along a longitudinal direction of the pump tube,
the pump unit being configured to squeeze out liquid within the pump tube,
wherein
the cassette comprises at least a portion of the pump unit, and
the device body comprises a further portion of the pump unit.

* * * * *